(12) United States Patent
Stoner

(10) Patent No.: US 10,674,768 B2
(45) Date of Patent: Jun. 9, 2020

(54) INDUCTION VAPORIZER AND METHOD

(71) Applicant: Charles S Stoner, Canton, OH (US)

(72) Inventor: Charles S Stoner, Canton, OH (US)

( * ) Notice: Subject to any disclaimer, the term of this patent is extended or adjusted under 35 U.S.C. 154(b) by 0 days.

(21) Appl. No.: 15/862,012

(22) Filed: Jan. 4, 2018

(65) Prior Publication Data

US 2018/0192701 A1     Jul. 12, 2018

Related U.S. Application Data

(60) Provisional application No. 62/443,613, filed on Jan. 6, 2017.

(51) Int. Cl.
| | |
|---|---|
| *A24F 47/00* | (2020.01) |
| *A61M 11/04* | (2006.01) |
| *H05B 6/10* | (2006.01) |
| *A61M 15/00* | (2006.01) |
| *A24F 5/00* | (2006.01) |

(52) U.S. Cl.
CPC ............ *A24F 47/008* (2013.01); *A24F 5/00* (2013.01); *A61M 11/042* (2014.02); *A61M 15/0025* (2014.02); *H05B 6/108* (2013.01); *A61M 2205/3368* (2013.01); *A61M 2205/368* (2013.01); *A61M 2205/3653* (2013.01)

(58) Field of Classification Search
None
See application file for complete search history.

(56) References Cited

U.S. PATENT DOCUMENTS

| 9,717,277 B2 | 8/2017 | Mironov |
| 2002/0078956 A1 | 6/2002 | Sharpe et al. |
| 2003/0230567 A1 | 12/2003 | Centanni et al. |
| 2012/0234315 A1 | 9/2012 | Li et al. |
| 2015/0320116 A1 | 11/2015 | Bleloch et al. |

FOREIGN PATENT DOCUMENTS

GB       347650        1/1931

*Primary Examiner* — Eric Yaary

(57) ABSTRACT

A method and apparatus for induction vaporization of an inhalable substance. Induction vaporization is achieved by placing at least one susceptor and a vaporizable substance into a container, and attaching the container to a cap having at least one leg. The container containing the vaporizable substance and the at least one susceptor, and the at least one leg of the cap are inserted through at least one opening on a plate or a housing such that the container and/or the at least one susceptor is at least partially located within an induction coil or electromagnetic (EM) field for heating.

26 Claims, 31 Drawing Sheets

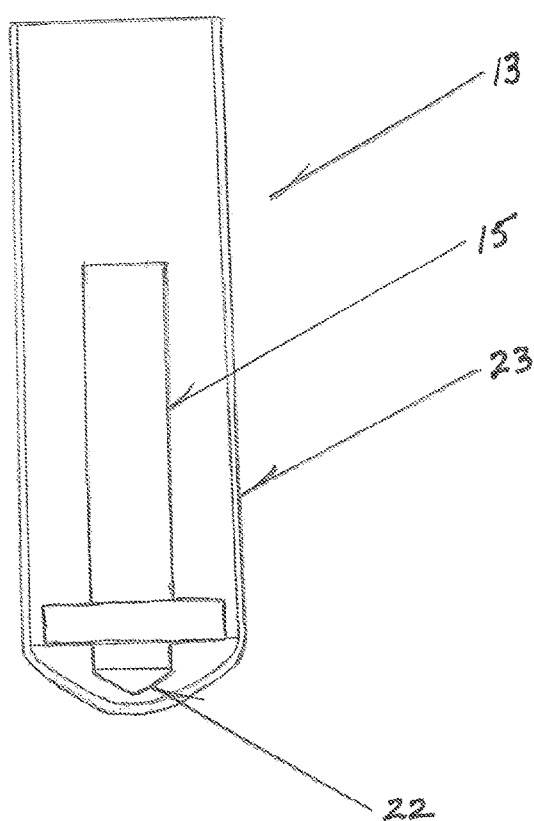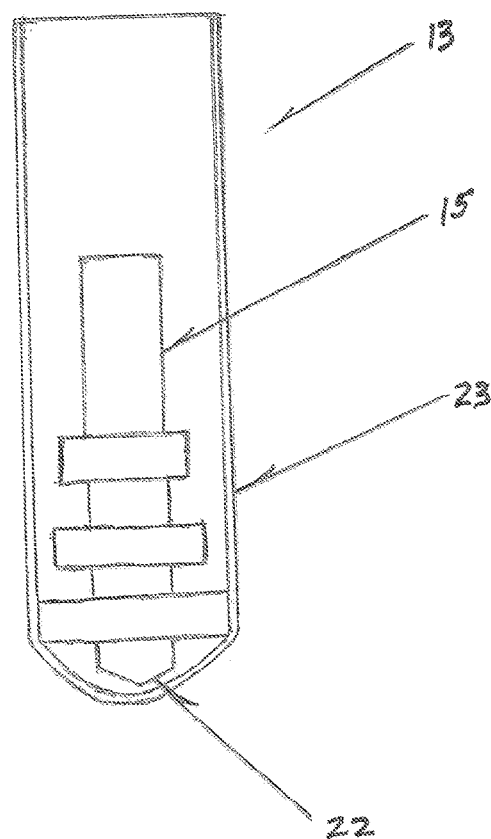

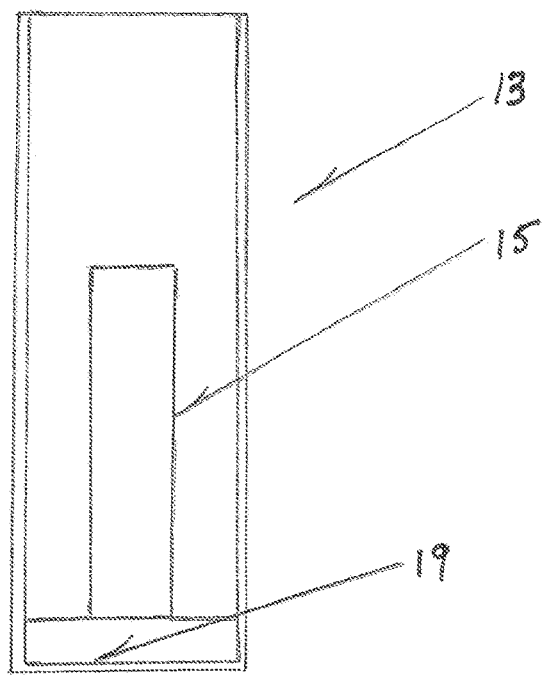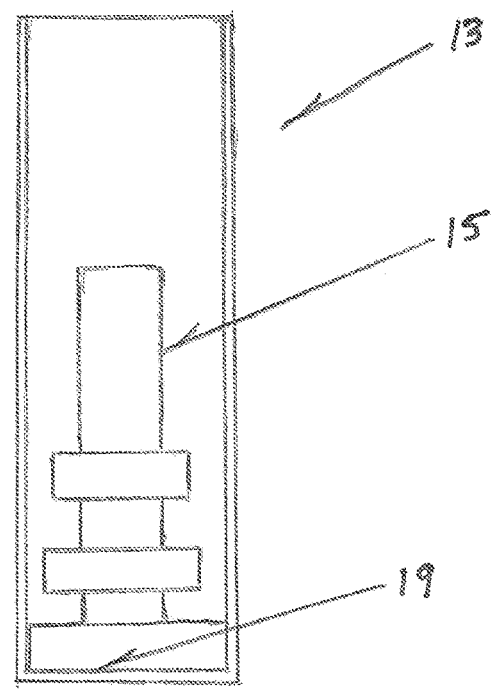

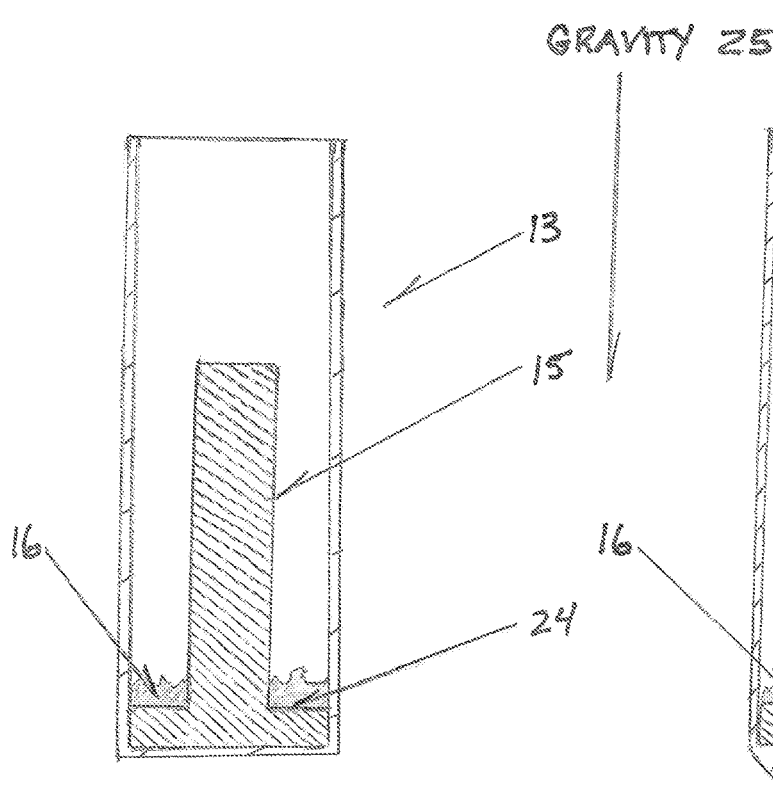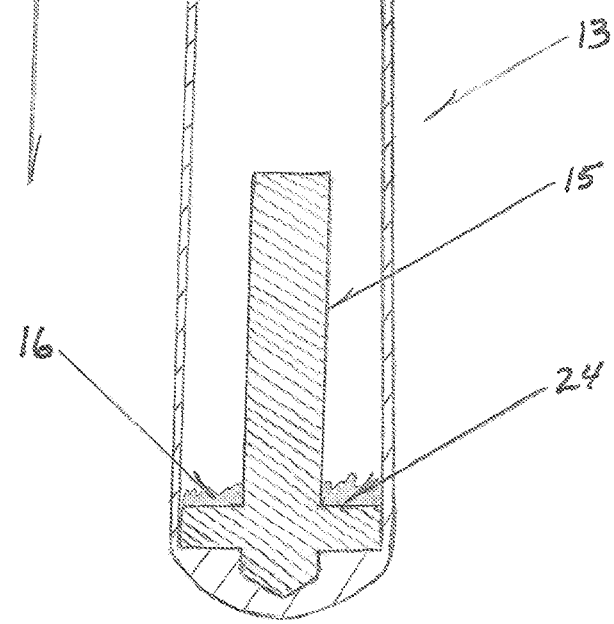

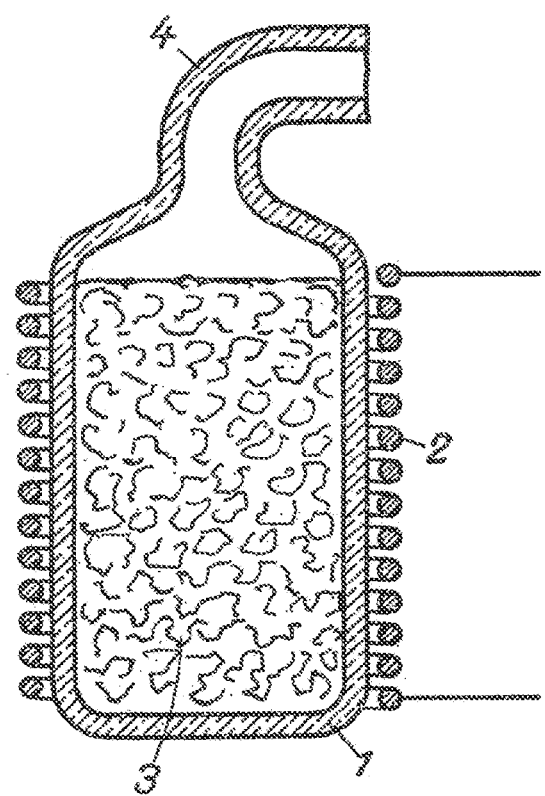

INDUCTION VAPORIZER AND METHOD

CROSS-REFERENCE TO RELATED APPLICATIONS

This non-provisional application claims priority to U.S. provisional application 62/443,613, filed on Jan. 6, 2017.

BACKGROUND OF INVENTION

The first induction vaporizer was disclosed at a convention in Germany on Oct. 26, 1928. Patent application GB 347,650 was subsequently filed in the United Kingdom on Oct. 22, 1929 and was printed for his Majesty's Stationary Office by Love & Malcomson, Ltd. in 1931. FIG. 46 of the instant application shows the prior art apparatus as it was published in 1931. In FIG. 46 a vessel provided with an outlet contains a liquid and metal, and is surrounded by an induction coil. The induction coil is connected to an alternating current (AC) supply and the metal is heated by eddy currents and/or magnetic hysteresis to transfer enough heat to the liquid to achieve vaporization.

BRIEF SUMMARY OF INVENTION

In the present invention the unique structure of the cap (3) when mated with the corresponding plate (28) or housing (2) allows a user to safely implement induction vaporization of an inhalable substance. Induction vaporization of an inhalable substance is achieved by placing at least one susceptor and a vaporizable substance into a container and then attaching the container to a cap having at least one leg. The container containing the vaporizable substance and at least one susceptor, and the at least one leg of the cap are then inserted through at least one hole or opening on a plate or housing such that the container containing the susceptor is at least partially located within an induction coil or exposed to an electromagnetic (EM) field for heating. The EM field produced by the induction coil generates hysteresis and/or eddy current(s) inside or on the skin of the at least one susceptor to thereby inductively heat the at least one susceptor and transfer heat to the vaporizable substance. The user inhales through a conduit to draw outside air through a vent hole that is in fluid communication with an opening in the container. The air mixes in the container with the heated vaporizable substance and forms an inhalable vapor. The vapor is drawn through a through-hole in the cap that is in fluid communication with the opening in the container.

The method and apparatus of the invention have the distinct advantage of separating the electrical paths, connections, and components from the vaporizable substance. In other words, the susceptor, which heats the vaporizable substance, has no direct electrical contact with the induction circuit. This reduces the number of materials in contact with the vaporizable substance, and reduces or prevents unwanted reactions or compounds from forming in the vapor. The apparatus and method also reduce the range of temperatures in contact with the vaporizable substance at the time of vaporization, provides precise and rapid control of heating, while heat is evenly distributed through the volume of the vaporizable substance. Therefore, the induction heating method and apparatus of the present invention achieves the desirable rates of vapor production with lower temperature gradients, lower peak temperature, and without the presence of hot spots, thereby producing a superior vapor quality. Furthermore, the container shapes disclosed herein when used with the susceptor shapes and compositions disclosed herein produce a superior inhalable vapor.

BRIEF DESCRIPTION OF DRAWINGS

Various exemplary embodiments of this invention will be described in detail, with reference to the following figures, wherein:

FIG. 10 shows a container with a pointed or conically shaped interior bottom surface mated with a complimentary susceptor having a pointed or conically shaped tip inserted therein;

FIG. 11 shows a container with a pointed or conically shaped interior bottom surface mated with a complimentary staged susceptor having a pointed or conically shaped tip inserted therein;

FIG. 12 shows a container with a flat interior bottom surface with a complimentary susceptor having a flat bottom surface inserted therein;

FIG. 13 shows a container with a flat interior bottom surface with a complimentary staged susceptor having a flat bottom surface inserted therein;

FIG. 14 shows a cross-section of a container with a flat interior bottom surface, a complimentary susceptor having a flat bottom surface, and a vaporizable substance contacting and/or resting on the floor of the susceptor;

FIG. 15 shows a cross-section of a container with a pointed or conically shaped interior bottom surface with a complimentary susceptor having a pointed or conically shaped tip, and a vaporizable substance resting on the floor of the susceptor;

FIG. 46 shows the prior art induction vaporizer apparatus of patent application GB 347,650 as it was printed in the year 1931.

DETAILED DESCRIPTION OF THE INVENTION

Figure 1:
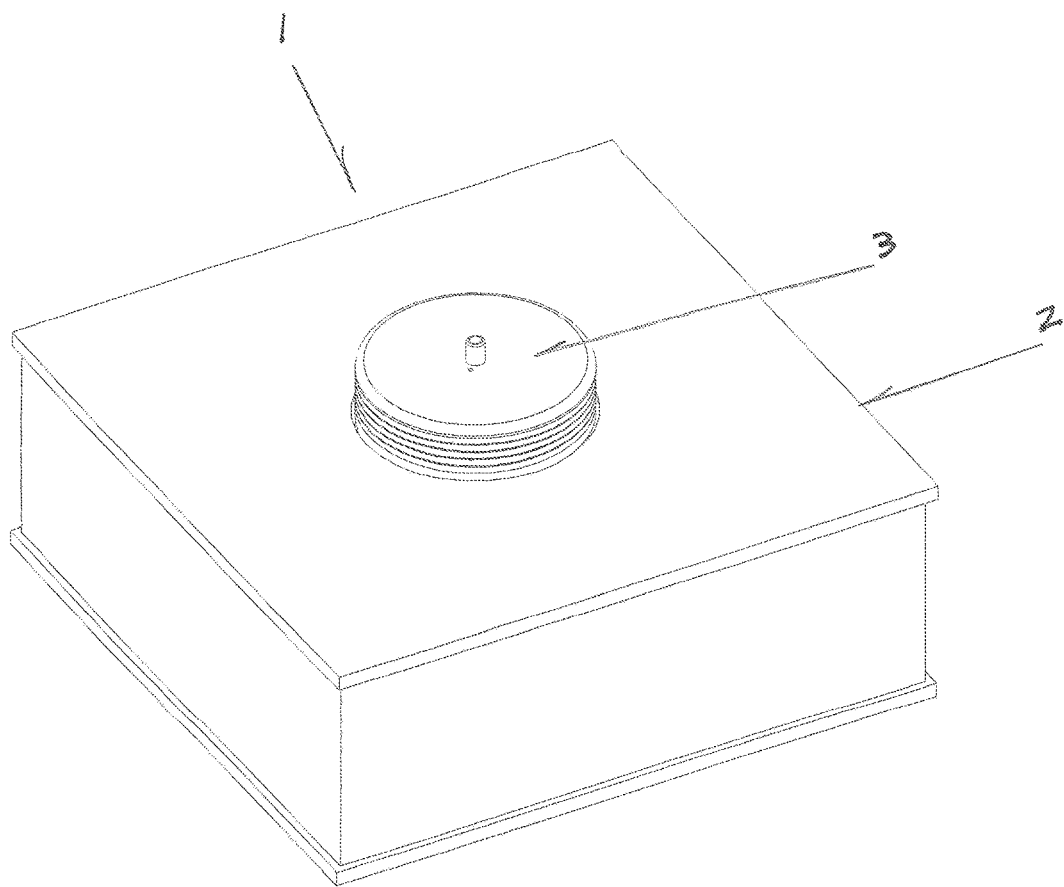
FIG. 1 shows the vaporization unit of the instant invention.
Figure 2:
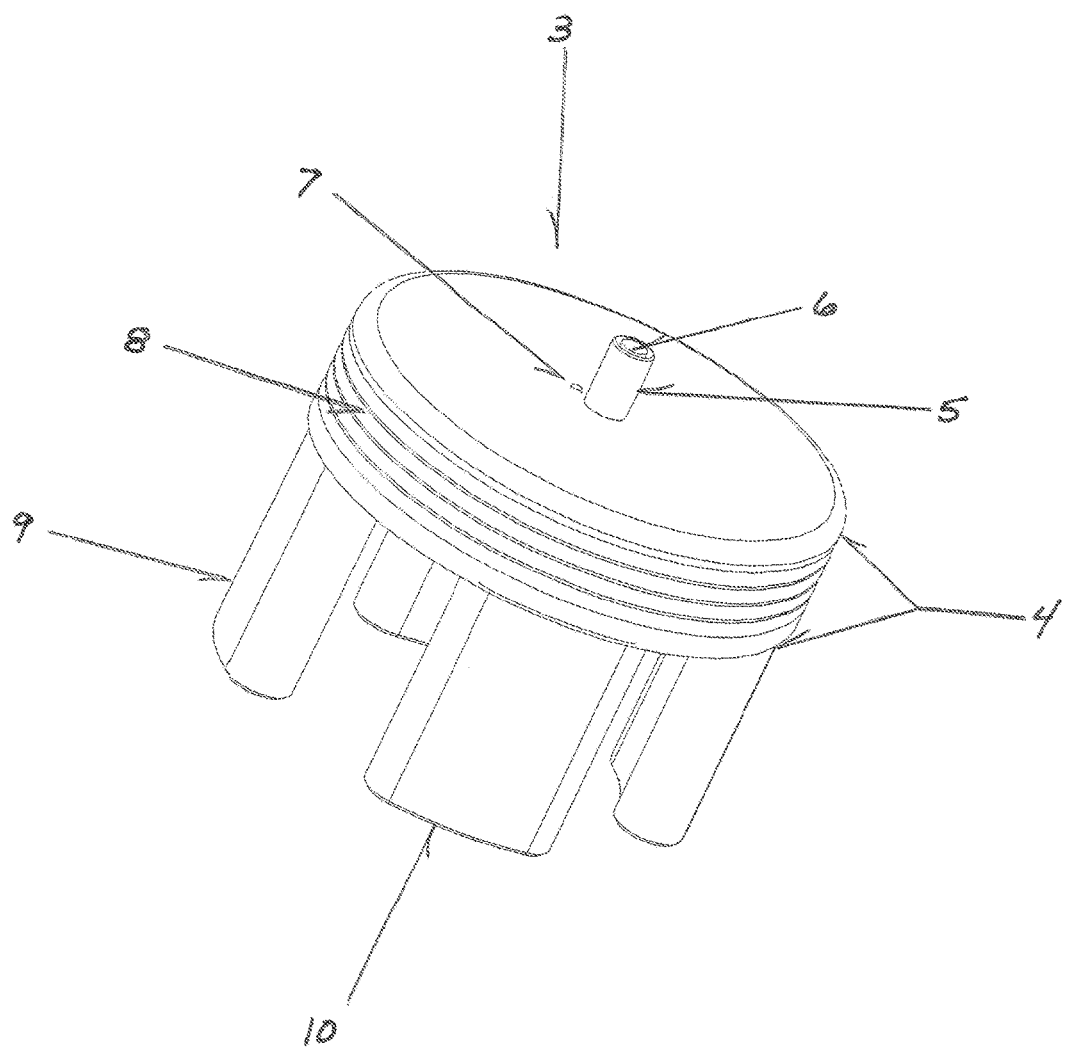
FIG. 2 shows the cap of the instant invention.
Figure 3:
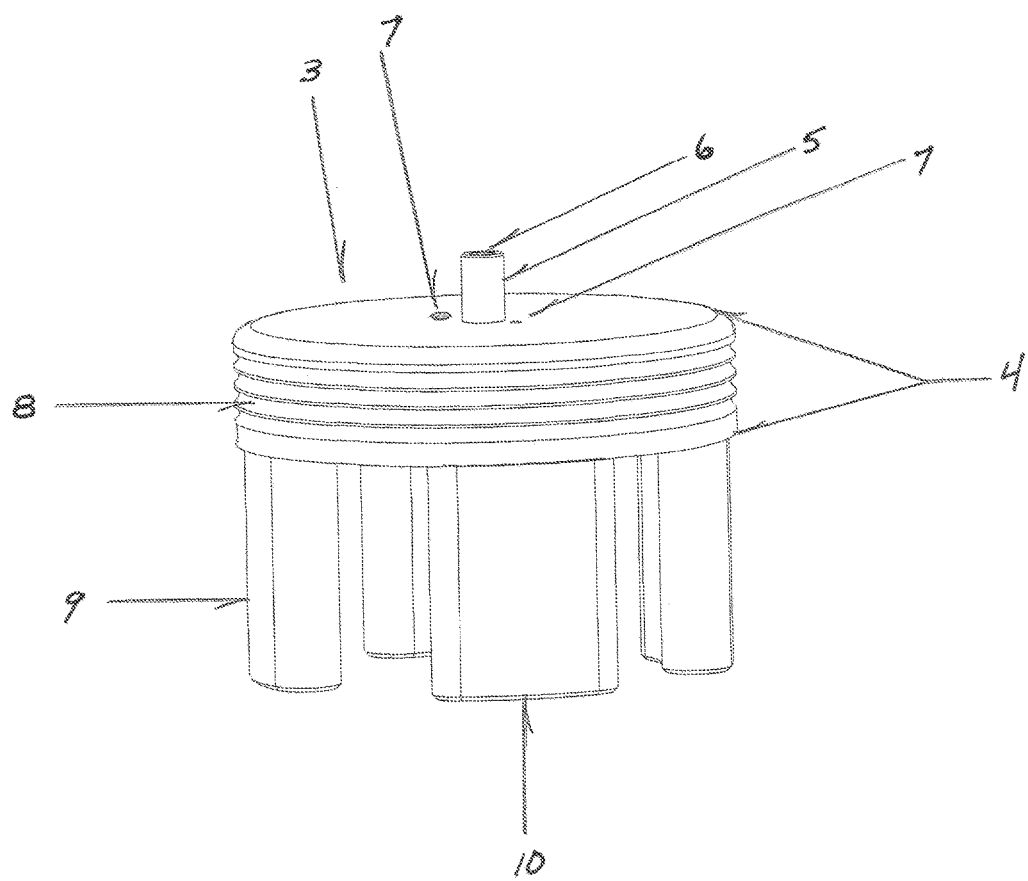
FIG. 3 shows another view of the cap of the instant invention.
Figure 4:
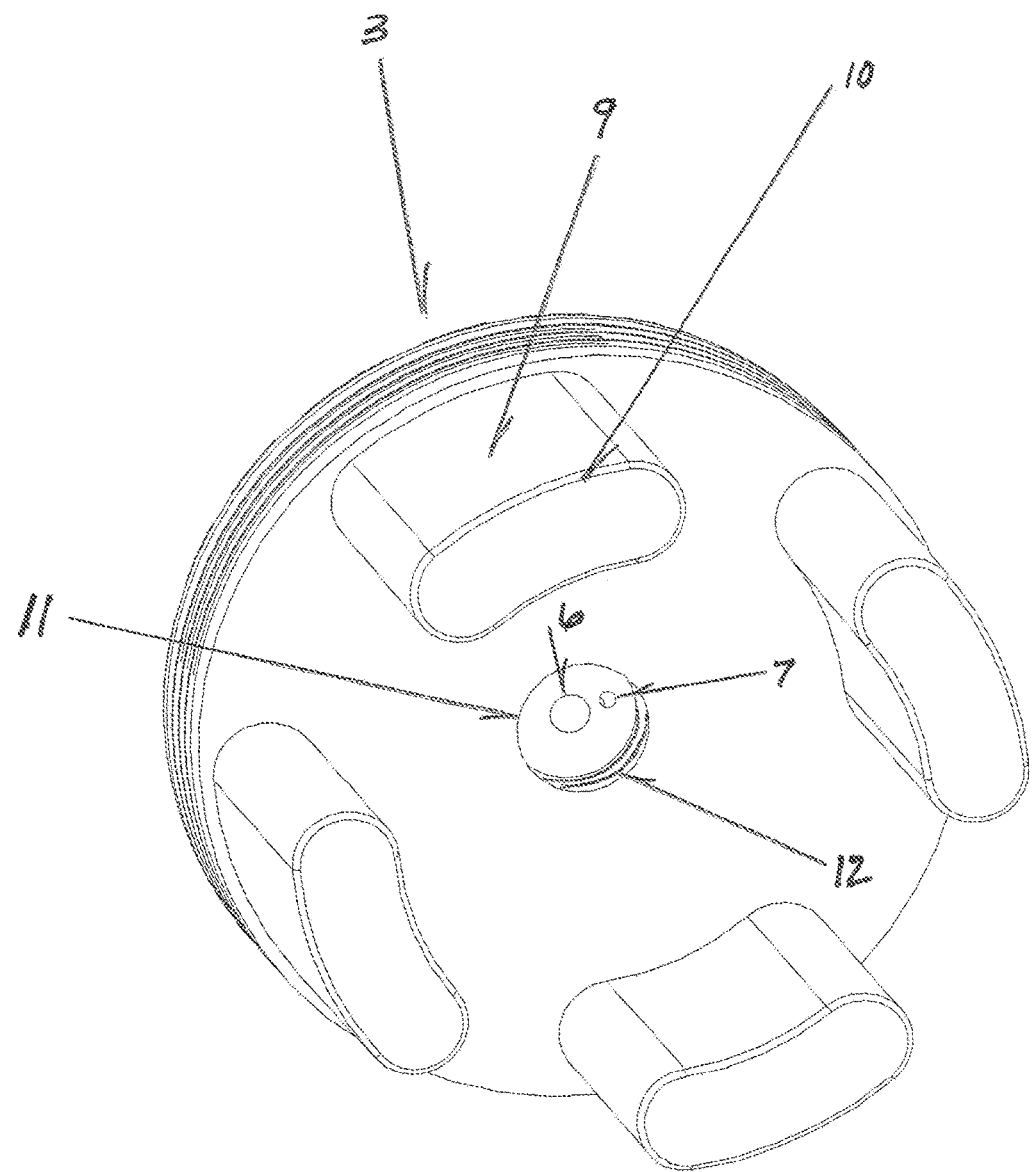
FIG. 4 shows the underside of the cap.

FIG. 1 depicts the vaporization unit (1) of the present invention. Vaporization unit (1) comprises a housing (2) and a cap (3). As shown in FIG. 1, the top of the cap (3) extends above the upper surface of the housing (2) in an upward vertical direction. The cap (3), as shown in FIGS. 2-3, comprises a body (4), at least one nipple (5) having a through-hole (6), at least one vent hole (7), ribs/grooves or texture (8), and at least one leg (9) with chamfer (10). FIG. 4 shows the underside of the cap (3) with a bore (11) having at least one thread (12). The cap (3) is preferably machined out of a billet of material, 3D printed, molded, and/or cast wherein elements (4)-(12) are integrally formed. Elements (4)-(12) of the cap (3) can also be formed out of separate pieces that are mechanically and/or chemically attached to one another. For example, the at least one leg (9) of the cap (3) and/or at least one nipple (5) can be integral to the body (4) or separate from the body (4). When the at least one leg (9) and/or at least one nipple (5) are separately formed from the body (4), the at least one leg (9) and/or at least one nipple (5) can be attached to the body (4) with a press-fit, shrink-fit, interference-fit, snap connection, quick connect-disconnect, at least one thread, soldering, brazing, welding, adhesives, or any other known mechanical and/or chemical manner. The cap (3) can be formed of any material or combination of materials that is able to withstand the generated heat. The top or side surfaces of the cap (3) can also include at least one channel or projection (not shown) that indicate the location(s) of the at least one leg (9) on a bottom surface of the body (4) of the cap (3).

Figure 5:
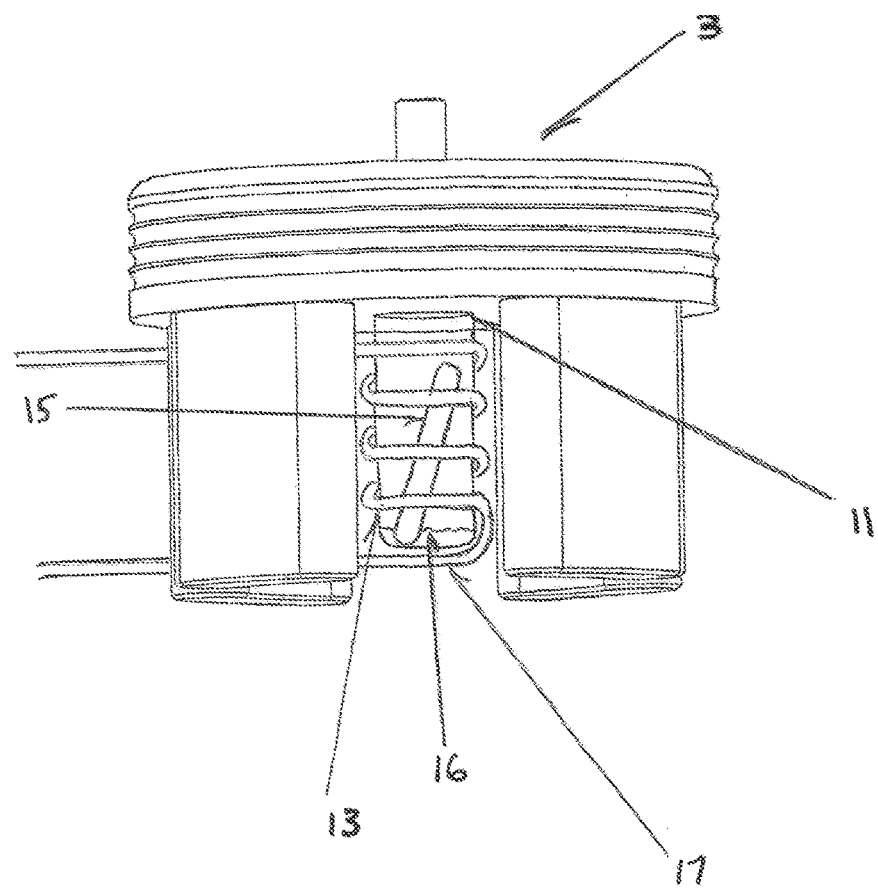
FIG. 5 shows a container inserted into the bore of the cap with an induction coil surrounding the container containing a susceptor.
Figure 6:
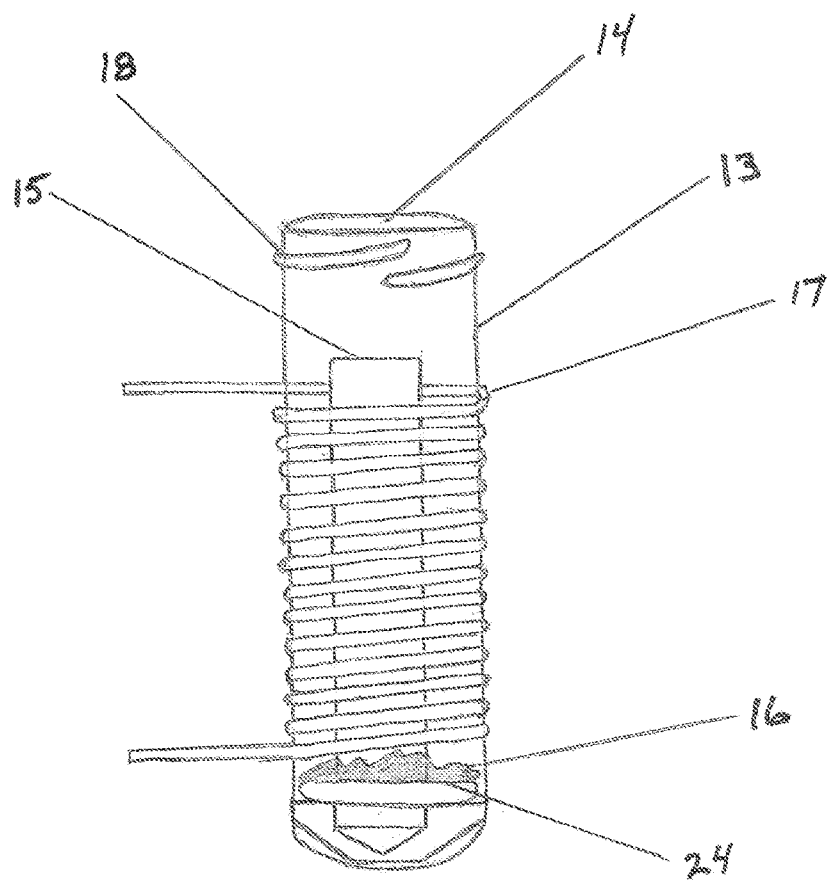
FIG. 6 shows a container containing a susceptor and a vaporizable substance surrounded by an induction coil, wherein the susceptor is substantially vertically and/or axially aligned in the container and induction coil.

FIG. 5 shows the cap (3) with container (13) inserted into bore (11), wherein the container (13) and a susceptor (15) are surrounded by an induction coil (17). The container (13) can be detachable, cleanable, refillable, replaceable, exchangeable, interchangeable, disposable or single use. The container (13), as shown in FIG. 6, has an opening (14), wherein the opening (14) is in fluid communication with the through-hole (6) and the at least one vent hole (7) of the cap (3). The container (13) holds the susceptor (15) and the vaporizable substance (16), and acts as an insulator between the susceptor (15) and induction coil (17). The container (13) may also have the induction coil directly built into or embedded within or on the material or sidewall(s) of the container. There is preferably an air gap between the container (13) and the induction coil (17) that serves as a thermal isolator. A smaller air gap provides more efficient power transfer, but less thermal isolation. If the induction coil (17) touches the container (13) the induction coil (17) can act as a heat sink.

The removability of the container (13) gives the user the ability to quickly swap vaporizable substances (16), susceptors (15), and/or containers (13). At least one opening (14) in the container (13) allows outside air to flow through vent hole (7) into the container (13), the air to mix with the vaporizable substance (16) thereby forming a vapor, and the vapor to be drawn out of the container (13) through through-hole (6) when the user inhales.

The container (13) can be made of any desired material that is able to withstand the temperatures of the susceptor (15). Suitable materials comprise glass, quartz, borosilicate, fiberglass, silica, ceramic, foamed ceramic, micropore ceramic, high temperature polymer, polytetrafluoroethylene, artificial fiber, natural fiber, nonmagnetic material, non-electrically conductive material, and combinations thereof.

The container (13) can have a neck, no-neck, shoulder, no-shoulder, flanged end, an unthreaded end, or a threaded end (18) that engages the bore (11). When the container (13) has a threaded end (18) with at least one thread, the at least one thread of the container (13) mates with the at least one thread (12) located in the bore (11), so that the container (13) can be screwed into the cap (3).

Figure 7:
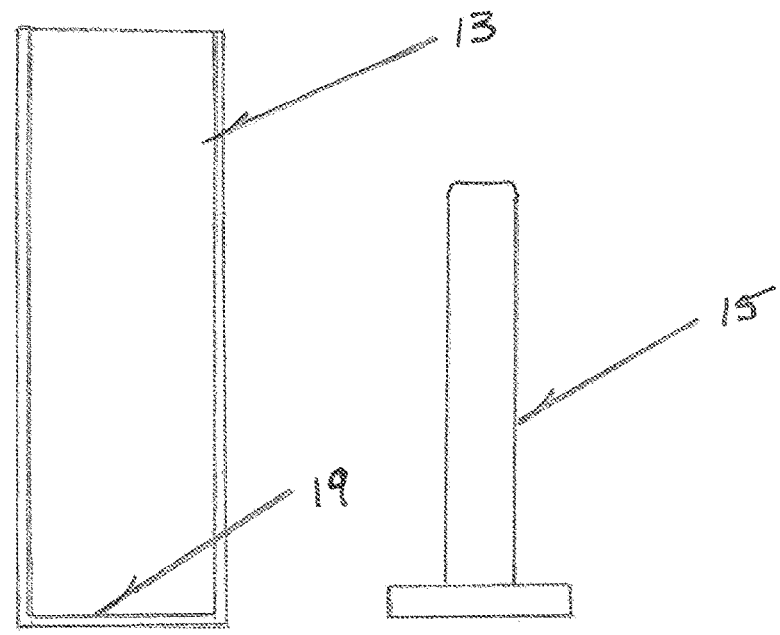
FIG. 7 shows a container with a flat interior bottom surface and a complimentary susceptor.
Figure 8:
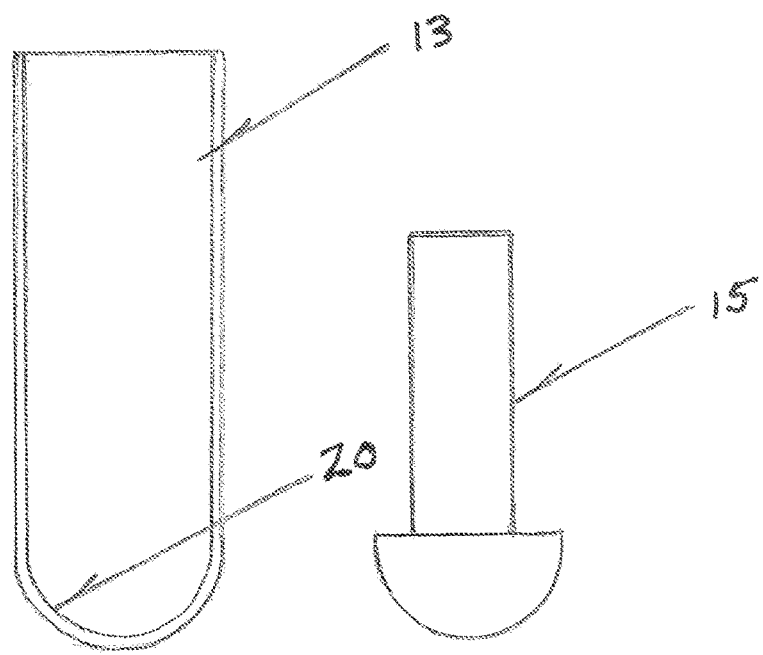
FIG. 8 shows a container with a concavely shaped interior bottom surface and a complimentary susceptor.
Figure 9:
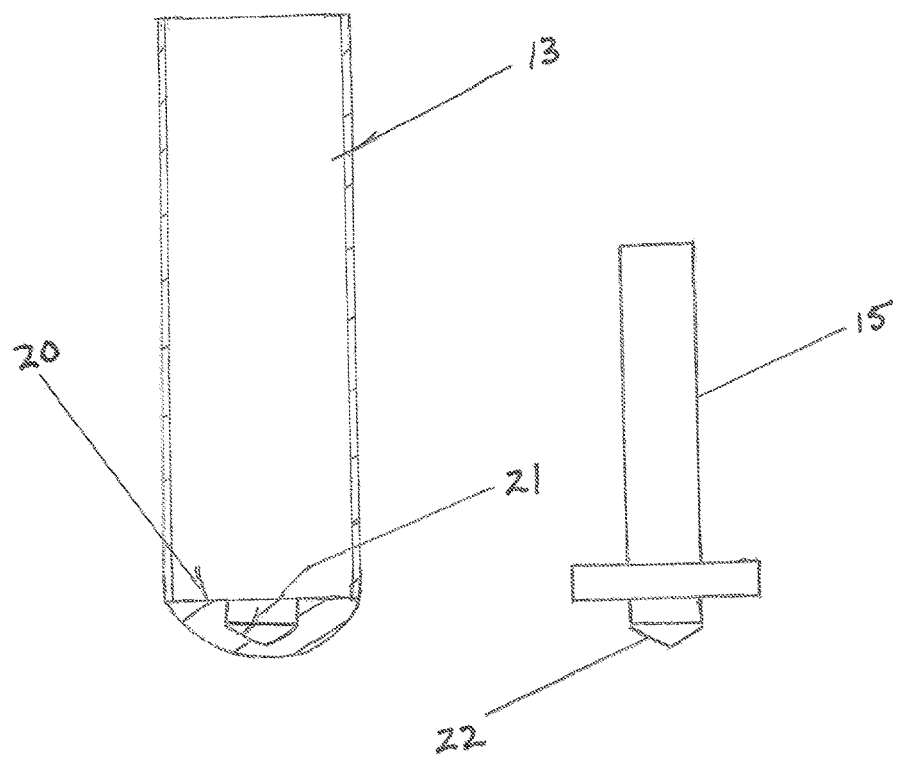
FIG. 9 shows a cross-section of a container with a pointed or conically shaped interior bottom surface and a complimentary susceptor.

The container (13) is generally a cylinder, however, the container can be any shape or size. The container (13) can have a flat interior bottom surface (19), as shown in FIG. 7, or a shaped interior bottom surface (20). FIG. 7 shows a complimentary susceptor (15) with a flat bottom surface for insertion into a container (13) having a flat interior bottom surface (19). FIG. 8 shows a complimentary susceptor (15) with a shaped bottom surface for insertion into a container (13) having a shaped interior bottom surface (20). Although the shape of the interior bottom surface can be of any shape, it is desirable to utilize a concave interior bottom surface, such as that shown in FIG. 8, to assist in centering the susceptor (15) within the container (13) and/or collecting vaporizable substance. FIG. 9 shows an interior bottom surface with a pointed or conical recess (21) that compliments and holds a pointed or conical tip (22) of susceptor (15). FIG. 9 also shows a container (13) having a shaped interior bottom surface (20) comprising a pointed or conical recess (21) that compliments and holds a pointed or conical tip (22) of the susceptor (15). A susceptor (15) is inserted into the shaped interior bottom surface (20) and/or recess (21) of the container (13) and the shaped interior bottom surface (20) and/or recess (21) holds the bottom end or tip (22) of the susceptor (15) in place. When a container (13) with a shaped interior bottom surface (20) and/or recess (21) is used in the cap (3) of the instant invention, at least a portion of the vaporizable substance (16) will pool or collect upon heating in the shaped interior bottom surface (20) and/or recess (21) due to melting and gravity. The susceptor (15) in FIG. 9 when viewed from top to bottom comprises an upper cylindrical shaft, a cylindrical disc, a lower cylindrical shaft, and a conical tip (22), wherein the upper cylindrical shaft is longer than the lower cylindrical shaft, and the cylindrical disc has a diameter larger than the upper cylindrical shaft and the lower cylindrical shaft. The upper cylindrical shaft and the lower cylindrical shaft may have the same or differing diameters. For example, the upper cylindrical shaft may have a smaller diameter than that of the lower cylindrical shaft. FIG. 10 shows the container (13) of FIG. 9 fitted or mated with a susceptor (15) having a pointed or conical tip (22), wherein the pointed or conical tip (22) substantially fills the pointed or conical recess (21), and the susceptor (15) is substantially vertically and/or axially aligned within container (13). FIG. 11 shows a container (13) having an interior bottom surface comprising a pointed or conically shaped recess fitted or mated with a staged susceptor (15) having a pointed or conical tip (22), wherein the pointed or conical tip (22) substantially fills the pointed or conical recess, and the staged susceptor (15) is substantially vertically and/or axially aligned within container (13). The staged susceptor can have any number or configuration of stages. FIGS. 12 and 13 show containers (13) with flat interior bottom surfaces (19) holding examples of complementary susceptors (15) inserted into the containers (13). The self-centering aspect of the susceptors (15) keeps the susceptor (15) substantially vertically and/or axially aligned in the container (13), prevents the susceptor (13) from contacting the sidewall (23) of the container (13), and promotes uniform heating of the susceptor (15) and/or vaporizable substance (16). A pointed or conical tip (22) can be added to susceptors (15) of various sizes and/or shapes to obtain the self-centering effect when used in conjunction with containers (13) having a pointed or conical recess (21). The pointed or conical tip (22) in other embodiments can be substituted with a projection or protuberance of any shape wherein there is a corresponding recess in the container (13), that is, a shaped projection or protuberance mates with a shaped recess in the container (13) to achieve self-centering. Likewise, the pointed or conical recess (21), in other embodiments, can be substituted with a recess of any shape wherein there is a complimentary projection or protuberance on the susceptor (15) to achieve self-centering in the container (13). A plurality of tips, projections or protuberances on the at least one susceptor and/or a plurality of recesses located in the container can also be used for self-centering or holding at least one susceptor in the desired position within the container. All susceptor shapes described herein may or may not include at least one tip, projection or protuberance. As mentioned above, the complementary shape of the susceptor (15) and the container (13) can act to center the susceptor (15) in the container (13), thus promoting uniform heating of the susceptor (15) and/or vaporizable substance (16).

In addition to the susceptor's (15) material composition, the size, shape and quantity of the at least one susceptor (15) can be adjusted to control heating of the vaporizable substance (16). The composition of the susceptor (15) may vary over the longitudinal length or transverse width of the susceptor to achieve the desired induction heating profile. A susceptor (15) can be any size or shape that produces vapor. Because the at least one susceptor can be any size or shape that produces vapor, a shaped interior bottom surface or a recess of the container is capable of holding more than one susceptor. Two or more susceptors (15) of any size or shape may be used in combination within the container (13) to control vaporization. If the susceptor (15) is too thick the magnetic field is unable to penetrate deep into the material, which requires an increase in power because a high conversion efficiency results, and the susceptor's thermal load, that is, the mass reduces the rate of thermal rise. If the susceptor is too thin, for example, much less than the skin depth, a low conversion of the magnetic field to heat energy via eddy current(s) occurs. Examples of different susceptor shapes include: ball, powder, wire, turning(s), scrap metal, pin, rod, cylinder, tube, pill, wedge, diamond, parallelogram, nail, screw, capsule, tablet, swiss cheese, bird's nest, egg, spin-top, fan, impeller, propeller, propeller mounted on a shaft, teardrop, bomb, rocket, missile, turbine, piston, bullet, arrow, spear, bowl, cup, coil, helix, auger, stepped, staged, bowling pin, snowman, hourglass, jacks toy, pyramid, conical, frustoconical, stellated hexahedron, stellated truncated hexahedron, stellated octahedron, stellated truncated octahedron, tetrahemihexacron, star, baseball bat, umbrella, crown, tree, tree branch, Christmas tree, alphabet letter, number, character, etc. The susceptor (15) may include at least one mounted or integral baffle, fin, disc, flux concentrator, or a combination thereof to transfer the desired heat to the vaporizable substance. The susceptor (15) can be shaped to move up and down inside the container, like a piston, upon inhalation. The susceptor (15) can also be shaped to spin, rotate, roll or revolve inside the container (13) during inhalation to stir the vaporizable substance (16). At least one cylinder, rod or pin shaped susceptor with at least one rounded and/or pointed end generally provides the best stirring action, however, the at least one susceptor may be of any shape that is capable of providing the described movement.

The at least one susceptor (15) can be fixed or attached to the container (13) in any known manner, however, it is preferable that the at least one susceptor (15) is loose and not mechanically fixed or coupled to the container (13) so that various susceptors (15) of differing shape, size, and material composition can be interchangeably swapped in the container (13) to meet the user's needs. Therefore, the at least one susceptor (15) rests on the inside bottom surface of the container (13) with the assistance of gravity. FIG. 14 shows a cross-section of a container (13) with a flat interior bottom surface, a complimentary susceptor (15) having a flat bottom surface, and a vaporizable substance (16) contacting and/or resting on the floor (24) of the susceptor. FIG. 15 shows a cross-section of a container (13) with a pointed or shaped recess, a complimentary susceptor (15) having a pointed or conically shaped tip, and a vaporizable substance (16) resting on the floor (24) of the susceptor. When the vaporizable substance (16) is placed into the container (13) and/or heated the vaporizable substance flows towards and contacts and/or rests on the floor (24) of the susceptor (15) with the assistance of gravity (25), as shown in FIGS. 14-15, without transferring the vaporizable substance (16) by wicking or capillary action. In other words, gravity (25) is used to deliver the vaporizable substance (16) to the bottom of the container (13) and the floor (24) of the susceptor (15). In this embodiment, capillary action, wicking, or surface tension are not used to transfer or draw the vaporizable substance (16) in a direction opposed to that resulting from gravity (25). Instead, the vaporizable substance (16) contacts and/or remains on the floor (24) of the susceptor (15) and/or interior bottom surface of the container (13) during induction heating. FIGS. 14-15 show the vaporizable substance (16) on a single floor (24) of the susceptor (15), however, susceptors can have more than one floor on which the vaporizable substance contacts and/or rests. FIG. 5 also shows an embodiment where gravity is used to deliver the vaporizable substance (16) to an interior bottom surface of the container (13) without the effects of wicking or capillary action on a solid cylinder susceptor (15) with two rounded ends. A susceptor of any shape and composition can also be used in the configuration of FIG. 5. In other embodiments, capillary action, wicking, and/or surface tension can be used to move, transfer or draw the vaporizable substance (16) in the desired direction. Known wicking or capillary action materials, such as foams, fibers, wires, meshes, screens, perforations, and/or twisted wires, are usable to achieve the desired wicking and/or capillary action. Freeze-casted or 3D printed titanium foams or cellular matrix materials are preferable wicking or capillary action materials.

A susceptor (15) comprises at least one material that can be inductively heated by an induction coil (17). The susceptor (15) material may comprise ferrous, non-ferrous, magnetic or non-magnetic metals or alloys, insulative or non-electrically conductive materials, or a combination thereof. The at least one susceptor (15) provides the source of heat that vaporizes the vaporizable substance (16). The inductively heatable materials, for example, can comprise conductive carbon such as graphite, tungsten, pure tungsten, 99.95% tungsten, electrically conductive ceramic, PTC ceramic, electrically conductive polymer, cobalt, cobalt superalloy, gold, silver, platinum, palladium, nickel, nickel superalloy, iron, cast iron, pure iron, carbon steel, stainless steel, 304 stainless steel, 304L stainless steel, 316 stainless steel, 316L stainless steel, 430 stainless steel, 430F stainless steel, austenitic stainless steel, ferritic stainless steel, martensitic stainless steel, duplex stainless steel, FeCrAl, copper, brass, bronze, aluminum, BCC/FCC mixed materials, and titanium, or a combination or alloy thereof. The susceptor (15) can also be a conductor and insulator composite, a ceramic matrix composite, a metal matrix composite, wherein the conductor can be metal, and the insulator can be glass, quartz, silica, ceramic or any other insulating material that is disclosed as being usable for the container. The susceptor may be a metal embedded or impregnated with an insulator, or an insulator embedded or impregnated with a metal. The insulator or metal may be partially or fully embedded or impregnated within the respective metal or insulator of the susceptor. For example, a metal wire or metal object can be fully encompassed by glass, so that only glass of the susceptor heats the vaporizable substance during induction heating. The wire or wires can also run around the outer periphery of the insulator and/or through the insulation, and can form a closed circuit or have two free ends. The susceptor may be a metal coated with an insulator or an insulator coated with a metal. The susceptor may also be a metal encased in an insulator or an insulator encased in a metal. When a metal susceptor is coated with an insulator, plasma enhanced chemical vapor deposition (PECVD) or any other known coating process may be used.

In another embodiment, the at least one susceptor comprises an insulating shell formed of any of the insulating materials disclosed herein and at least one loose conductive or metal yoke formed of any of the conductive or metal materials disclosed herein. The at least one loose yoke is positioned inside the insulating shell and movable inside the insulating shell. Gravity will sit the yoke on the bottom inner surface of the shell. The outer periphery of the at least one yoke is smaller than the inner periphery of the insulating shell which allows for thermal expansion of the at least one yoke upon heating. The shape, size and composition of the at least one yoke and/or shell can be adjusted either individually or in combination to obtain the desired heating profile. A gap or space between a portion of the at least one yoke and the shell can also be adjusted to obtain the desired heating profile. The shell can be of any shape or size and can have any thickness, while the yoke can be of any shape or size that fits within the shell.

A susceptor (15) is preferably formed into the desired shape by machining a billet of material, 3D printing, molding, and/or casting. Solid or non-solid, or solid and non-solid material combinations are usable as the susceptor material. Non-solid materials include porous and foamed materials. The non-solid material can also include meshes, screens, perforations, and/or twisted wires that may or may not act as a wick and maybe formed into any of the shapes disclosed herein. Hollow susceptors having at least one solid and/or non-solid wall are also usable. Steel, stainless steel, and cast iron may be used as ferrous susceptor materials. The method and apparatus of the present invention are preferably used with low-carbon steel, mild-carbon steel, high-carbon steel, stainless steel, cast iron, pure iron, tungsten, titanium or titanium alloy susceptor materials, or a combination thereof. Grade 2 titanium and 99.95% tungsten are the most desirable susceptor materials due to their inert nature and ability to deliver the best taste. Another advantage of using titanium or tungsten as a susceptor material is that titanium and tungsten only inductively heat through eddy current(s), which allows a slower and more controlled heating profile. Other non-magnetic and non-ferrous materials can also be inductively heated solely by eddy current(s) to generate the heat necessary for vaporization. Materials that inductively heat through eddy current(s) and hysteresis in combination heat more rapidly.

In another embodiment, the container (13) can be constructed out of an inductively heatable material, wherein the container itself acts as the susceptor. At least one susceptor and/or insulator can also be placed into the inductively heatable container thereby increasing control over the heating process. Inductively heatable containers with insulative interior and/or exterior coating(s), such as glass, silica ($SiO_2$), or ceramic, are also suitable for use in the disclosed method and apparatus. PECVD or any other known coating process may be used to apply silica or another coating composition to a glass, ceramic, metal, or composite container. Composite containers comprising the materials listed above are also capable of being used as the susceptor. A PECVD layer when applied to the interior of the container can improve wetting of the vaporizable substance (16) on the interior surface of the container (13).

The at least one susceptor may be partially or entirely located within the induction coil or EM field. FIG. 6 shows an embodiment where the susceptor (15) is partially located in the induction coil (17). When heating a susceptor with a pointed or conical tip it is preferable to avoid heating the tip directly with electromagnetic energy. Induction heating the tip, or a sharp corner directly may create a hot spot that could heat the vaporizable substance to a higher temperature than desired. However, at least one tip, point or corner of a susceptor may be located within the induction coil and directly inductively heated to focus the desired amount of heat into the vaporizable substance in a controlled manner. Using at least one rounded, curved or radiused end, edge, side and/or corner is also effective in preventing the formation of hot spots in the susceptor. Adjusting the position and/or amount of the at least one susceptor (15) within the induction coil (17) and/or EM field can be used to vary and control the heating profile of the susceptor (15).

Figure 16:
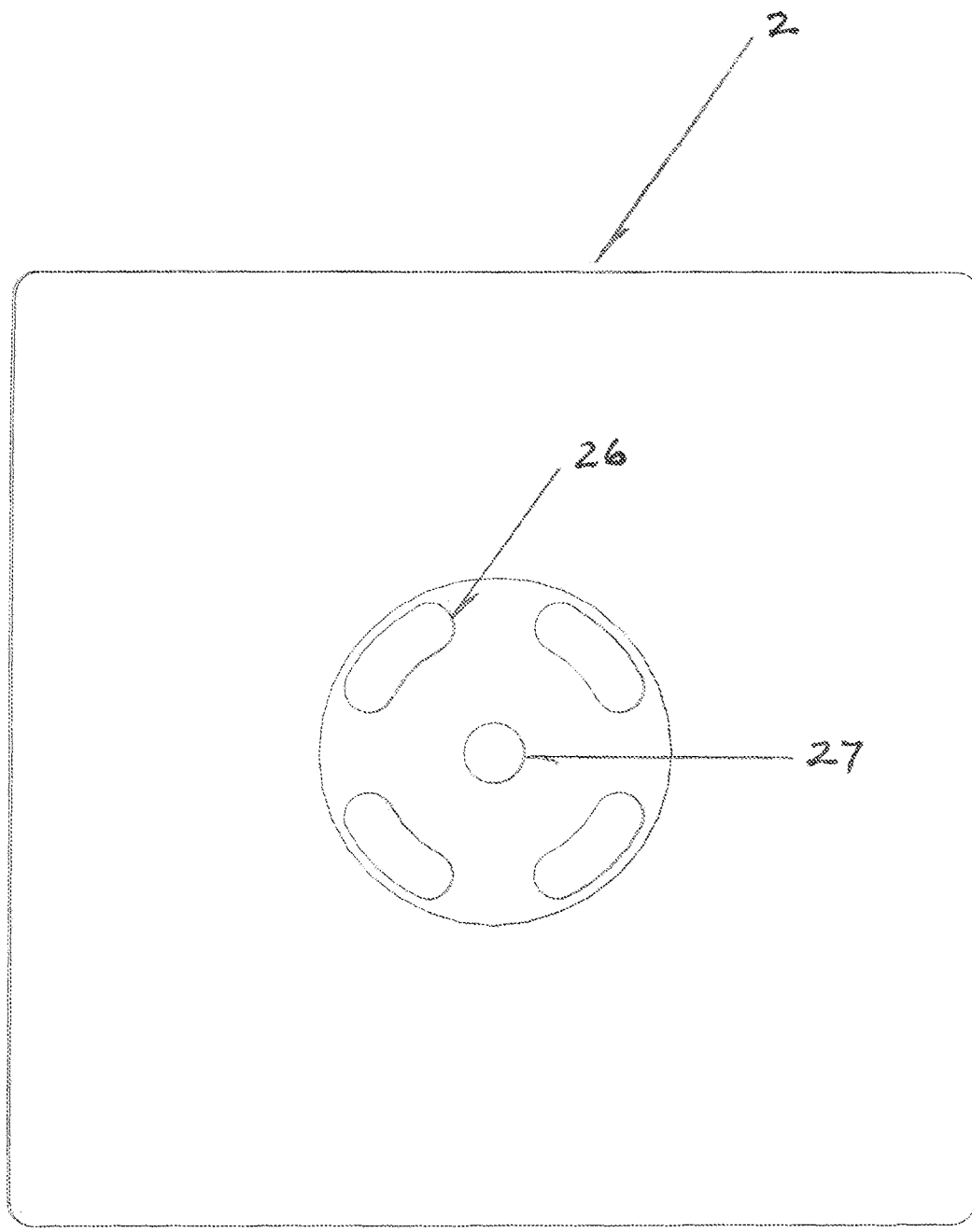
FIG. 16 shows a top view of a housing with corresponding openings for the at least one leg and container.

FIG. 16 shows a housing (2) with an associated or corresponding at least one outer opening (26) for the at least one leg (9), and a central opening (27) for the container (13). At least one susceptor (15) is placed into a container (13), a vaporizable substance (16) is placed into the container (13), and the container (13) containing the vaporizable substance (16) and the at least one susceptor (15) is attached to cap (3) having at least one leg (9). The at least one leg (9) and the container (13) containing the at least one susceptor (15) and the vaporizable substance (16) are inserted through openings (26) and (27) on a top plate or housing (2), respectively, such that the container (13) and/or at least one susceptor (15) are at least partially located inside the induction coil (17). In other words, the at least one leg (9) and the container (13) mate with openings (26) and (27), respectively. Because the at least one leg (9) extends farther from a bottom surface (32) of the body (4) of the cap (3) than the container (13) extends, as shown FIGS. 5, 20, 25, 26 and 27, the at least one leg (9) acts as a stand-off for the container (13) when the bottom of the at least one leg (9) is placed on a surface, such as a table, countertop, or floor. The greater extension of the at least one leg (9) when compared to the extension of the container (13) also results in the at least one leg (9) being inserted into the plate (28) or housing (2) before the container (13). Therefore, the at least one leg (9) and the corresponding at least one opening (26) for the at least one leg work together during mating to center the container (13) and/or susceptor (15) within the central opening (27) and/or induction coil (17). The container (13) containing the susceptor (15) and the vaporizable substance (16) are suspended from the cap (3) and at least partially positioned within an induction coil and/or EM field. In another embodiment, the container (13) and at least one leg (9) can be inserted through a single hole or opening on a top plate or housing (2). The induction coil (17), which is inductively coupled to the at least one susceptor (15) within the container (13), surrounds the container (13) containing at least one susceptor (15), and the at least one susceptor (15) is heated by magnetic hysteresis and/or eddy current(s) produced by the induction coil (17). The at least one susceptor (15) transfers heat to the vaporizable substance (16) by direct or indirect conduction, radiation, or convection which causes the vaporizable substance to be converted to vapor when mixed with air.

Figure 17:
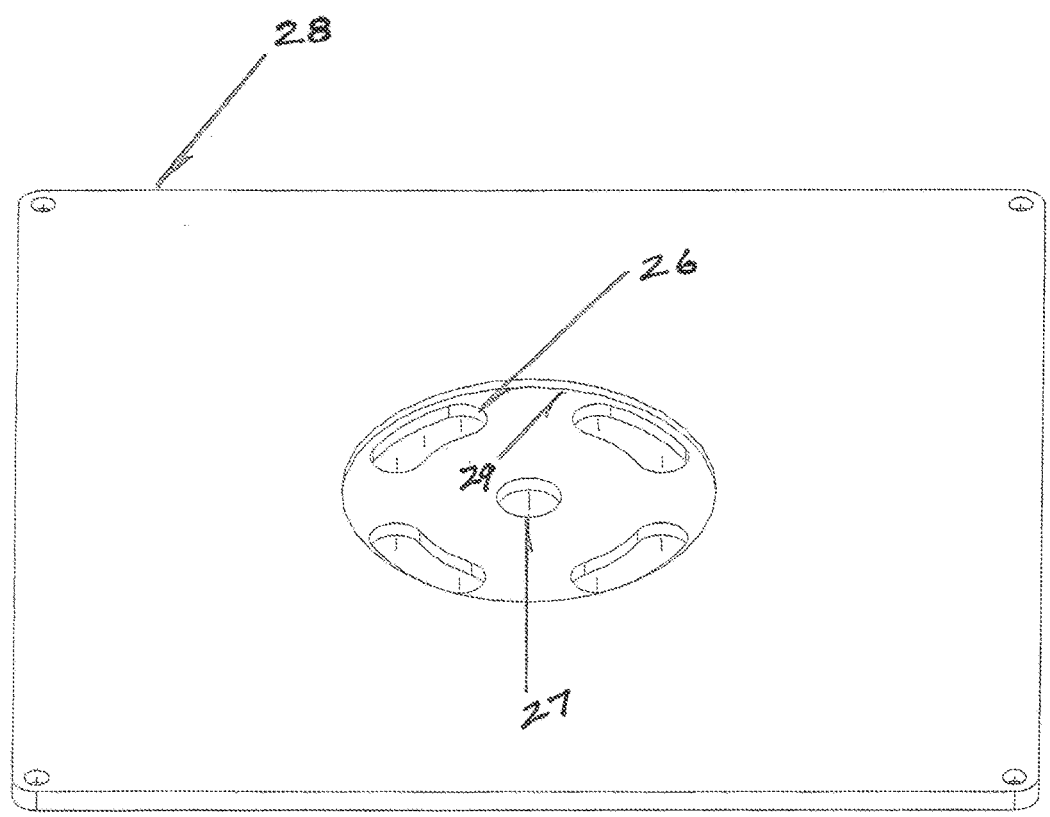
FIG. 17 shows a top plate with corresponding openings for the at least one leg and container, and a cavity that receives a body of the cap.

FIG. 17 shows a perspective view of a top plate (28) of the housing wherein at least one outer opening (26) for the at least one leg (9), and a central opening (27) for the container (13) are present. Also present in FIG. 17 is an optional cavity (29) in which the body (4) of the cap (3) can be inserted. The cavity (29) in conjunction with the opening(s) (26) and (27) work to align the cap (3) and positionally center the container (13) within the induction coil (17). The orientation or layout of the at least one opening (26) for the at least one leg (9), and opening (27) for the container (13) can be in any configuration and is not limited to that shown in FIGS. 16-17. Inside the housing (2) the outer periphery of the at least one leg (9) and the corresponding at least one outer opening (26) of the plate (28) or housing (2) may be surrounded or fenced by a cage (not shown) that is coaxial, concentric, or axially aligned with the central opening (27), induction coil (17), container (13), and/or at least one susceptor (15). This arrangement results in the at least one leg (9) being positioned between the cage and the induction coil (17) and/or the container (13). When a tubular cage is used in conjunction with the cavity (29), the tubular cage is substantially located under the cavity (29) and the cage may have a circumference or diameter that is the same, smaller, or larger than the circumference or diameter of the cavity (29). The cage may be a solid or perforated sheet of any material that is bent or formed into a complete tubular cage wherein the opposing ends are mechanically and/or connected, or an incomplete tubular cage wherein the opposing ends are not mechanically and/or chemically attached. Any size gap or space can be used between the opposing ends of the sheet material that form an incomplete tubular cage. In another embodiment, the cage is a seamless solid or perforated tube of any material. The cage can be of any geometric shape and have any length, height and/or thickness that fits within the housing. The cage may contact and/or be mounted to the top and/or bottom plate(s) or portion(s) of the housing (2). Therefore, the cage may partially extend any distance within the housing (2) from the top and/or bottom plate or portion of the housing (2), or the cage may extend completely through the interior of the housing (2) wherein the top and bottom plates or portions of the housing (2) sandwich the cage. The cage may also be recessed in at least one corresponding groove in the top and/or bottom plate(s) or portion(s) of the housing (2). Perforations and/or margins of any shape, pattern, size and/or quantity in any combination can be used on the cage to achieve the desired percentage of open area for venting the induction coil (17) and/or the container (13) containing the at least one susceptor (15).

Figure 18:
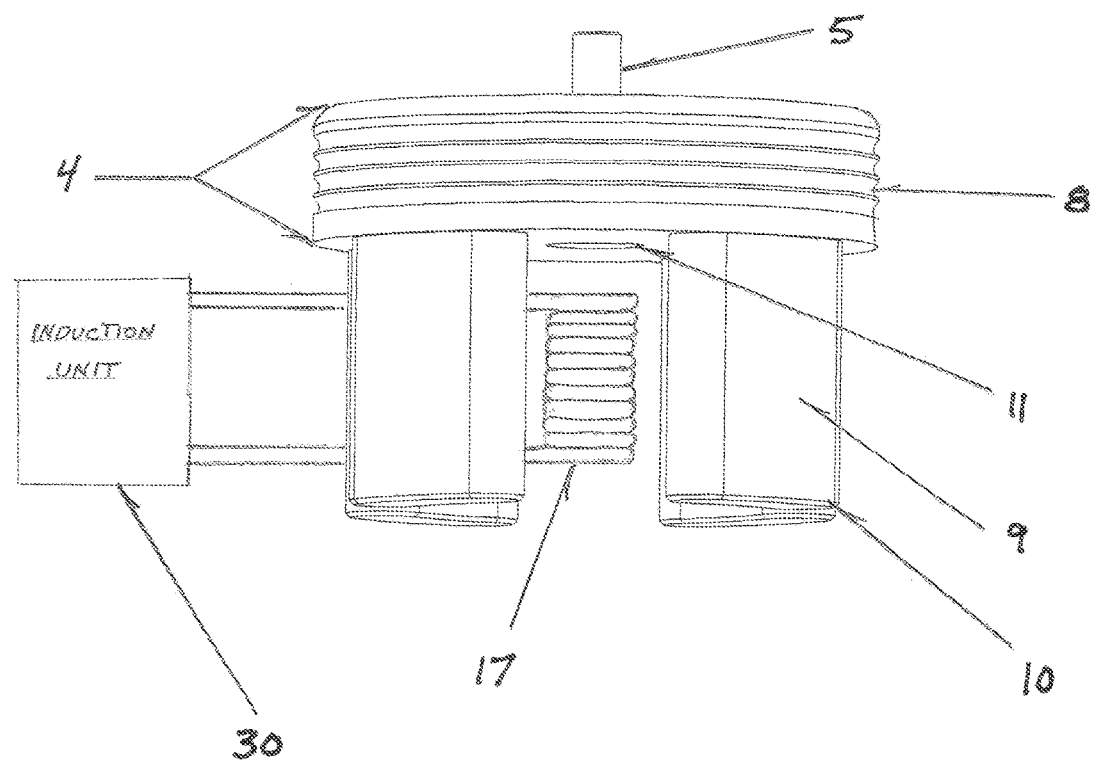
FIG. 18 shows an induction coil extending between the legs of the cap to a position under a bore with an induction unit powering an induction coil.

An induction unit (30), shown in FIG. 18, produces an alternating EM field in the induction coil (17) which induces heat generating magnetic hysteresis and/or eddy current(s) in the at least one susceptor. The at least one susceptor in turn heats the vaporizable substance (16) located in thermal proximity thereto to produce a vapor when turbulent air contacts the vaporizable substance (16). In other words, the at least one susceptor (15) is close enough to the vaporizable substance (16) to transfer heat thereto. The susceptor (15) is in thermal proximity, layered on, interposed in, or surrounded by the vaporizable substance (16). Any AC switching frequency can be used for the alternating EM field that achieves the desired heating effect, that is, a suitable frequency that matches the desired skin depth of the electromagnetic penetration. High frequency for thin walls, and low frequency for thick walls. FIG. 18 shows the leads of an induction coil (17) running to the side of the cap (3), however, the leads of the induction coil (17) can be run vertically downward. The induction unit (30) can be positioned at a side of the cap (3) or under the cap (3).

The induction coil (17) and/or induction unit (30) may be at least partially embedded or encapsulated in a non-conductive insulating material for mechanical and/or chemical attachment to the housing. Embedding or encapsulating the induction coil (17) significantly increases strength, durability and reliability. Flexible wires and/or electrical connectors may be used to connect the embedded or encapsulated induction coil to the induction unit (30) that generates a switching AC. The embedded or encapsulated induction coil comprises a hole located within an inner space formed by the windings of the induction coil. Preferably there is a layer of insulating material on the interior surface of the coil forming a wall of the hole. The hole in the insulating material is sized to allow a container (13) to be at least partially positioned within the induction coil (17). The hole in the insulating material of the embedded or encapsulated induction coil may be formed concurrently with the molding or casting process that is used for embedding or encapsulating the induction coil. Alternatively, the hole may be drilled in the insulating material after the embedding or encapsulating process. Resins, polymers, glasses, ceramics and any other insulating materials listed herein may be used either alone or in combination to form an embedded or encapsulated induction coil.

Operation of the induction unit (30) can be continuous, pulsed, or intermittent with fixed or variable time periods during heating. A pulse width modulator, on/off switch(s), and/or analog or digital timers, such as single shot, interval, or off-delay timers, in the circuit can be used to control the heating period(s). The pulse width modulator, on/off switch (s), and/or analog or digital timers can be used to control AC or DC, and can be placed before or after the power supply or anywhere in the electrical circuit prior to the induction unit (30). Using a timer allows the user to deliver a predictable and repeatable dosage of vapor. The amount of voltage, current, and/or power delivered to the induction unit (30) can be controlled to adjust the heating profile of the susceptor (15). Conventional controllers and processors can be used to dynamically control the power. Vaporization of the vaporizable substance (16) can be controlled by the adjustment of time, power, and/or AC switching frequency either individually or in combination.

The number and density (spacing) of the windings of the induction coil (17) can also be adjusted to achieve the desired heating effect, that is, more or less heating over the length of a susceptor (15). Multiple coils may be used at the same or at different frequencies along the length of the container (13) and/or susceptor (15) which can be mutually or individually controllable to obtain the desired heating effect or heat gradient profile. Multiple coils can also be used to move a hot zone along the length of a susceptor (15) in time or to provide a time dependent heating profile. The induction coil (17) can be of any shape or size corresponding to the shape or size of the container (13) and/or susceptor (15).

The at least one leg (9) of FIGS. 2-5 and 18-28, which can be of any number, act to:
1) protect the container;
2) prevent the container when hot from contacting the user or any undesirable surface, such as a table, countertop, or floor;
3) serve as a key or indexing means when inserted into the at least one opening on the top plate or housing, so that the at least one leg does not contact the coil regardless of the orientation in which the cap is inserted into the top plate or housing and the container and/or susceptor are centered in the induction coil;
4) serve as a base and prevents the cap from tipping over;
5) serve as a heat shield to shield electronic components from radiant heat coming from the susceptor and/or container; and/or
6) serve as an electromagnetic shield when constructed of a shielding material, such as ferrite, to prevent magnetic field from escaping the coil and cap region.

In FIGS. 2-5 and 16-19 a configuration of four legs (9) are used as the at least one leg (9). The at least one leg (9) can be formed of any material or combination or materials, and can be in the form of any geometric shape. The at least one leg (9) can be stepped inward from the outer circumference of the body (4), as shown in FIGS. 2-5 and 18, or can be flush, or extend outward from the outer circumference of the body (4). When the at least one leg (9) is inserted into at least one opening (26) of the top plate (28) or housing (2), the bottom of the at least one leg (9) proximal to the optional chamfer(s) (10) may or may not contact a support surface or housing (2). The at least one leg (9) may hang in the housing (2) or may only extend partially through the at least one opening (26) or cavity (29) of the housing (2). In another embodiment, it is also possible to utilize a legless cap with a conventional indexing means, however, the advantages of using at least one leg (9) are not present in a legless design.

At least one vent hole (7) creates a pathway from an outer surface of the cap (3) to the bore (11), in which the container (13) is inserted. The air, which is drawn in from the at least one vent hole (7), then contacts the vaporizable substance (16) that is heated by the at least one susceptor (15) and as air mixes with the heated vaporizable substance (16) a vapor is created. At least one vent hole (7) having a predetermined diameter and entry angle provides the desired airflow to the opening (14) of the container (13). A plurality of vents (7) with the same or different diameters and the same or different entry angles can be used to adjust the mixture of air and vaporizable substance. The at least one vent (7) can also be in the shape of a funnel. When the cap (3) is formed with a plurality of vent holes (7), the user can plug the desired vent holes (7) in any configuration to obtain the desired effect. FIG. 2 shows a vent (7) located in the top surface of the cap (3), however, the at least one vent hole (7) can alternatively be located on the side or bottom surfaces of the cap, or a combination of surfaces. The at least one vent (7) is preferably at an angle to aid in mixing air with the vaporizable substance (16) or provide the desired turbulence within the container (13). The angle can be adjusted to form a vortex or venturi effect within the container (13). The vortex in some instances is able to spin, rotate, roll or revolve the at least one susceptor (15) within or around the inside of the container (13) during inhalation. This effect helps stir the vaporizable substance (16) during the inhalation process. The at least one vent (7) can also be in the form of a needle valve and/or a threaded plug in which the size of the opening and/or airflow can be adjusted.

The vaporizable substance may be a liquid, gas, gelatin, semi-solid, solid, wax, oil, essential oil, resin, live resin, rosin, dewaxed substance, winterized substance, distillate, or concentrate that produces an inhalable vapor or aerosol delivering the user with the desired effects and/or taste. The container (13) can be filled with a vaporizable substance (16) by supplying a vaporizable substance (16) through the container opening (14). The container (13) can be filled with the container (13) detached from the cap (3), and alternatively with the container (13) already attached to the cap (3) by supplying a vaporizable substance (16) through at least one vent (7) or through-hole (6). When the container (13) is loaded with vaporizable substance with the container (13) attached to the cap (3), the cap (3) and/or container (13) can be previously inserted into the housing (2) or freestanding. The desired fill level of the container is determined by the user's needs. Prefilled containers may also be used with the disclosed method and apparatus. The induction coil (17), the container (13), and/or the at least one susceptor (15) can additionally be unitary and replaced as needed.

Figure 19:
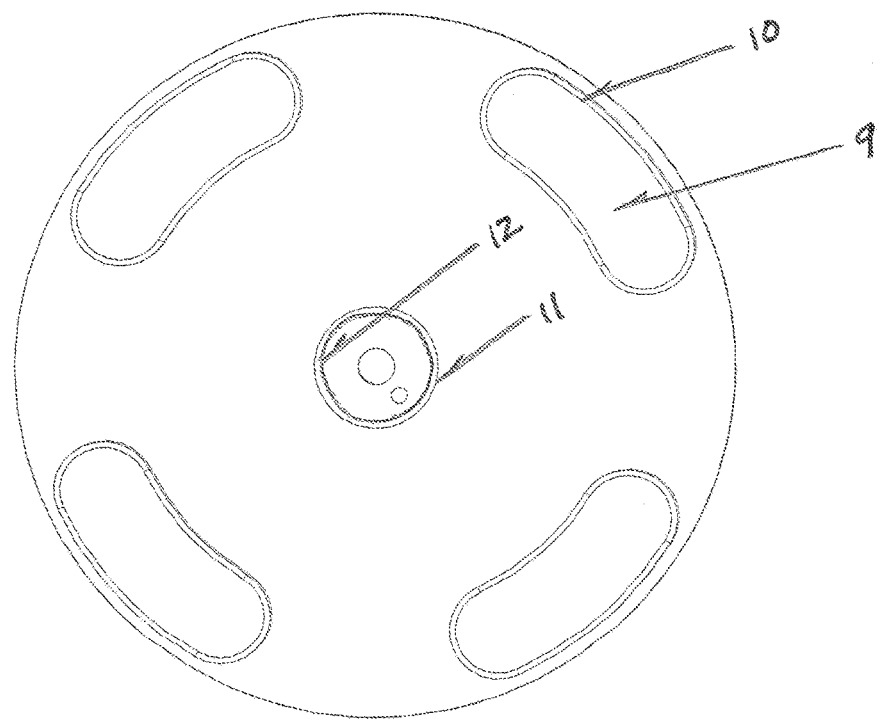
FIG. 19 shows a bottom view of the cap.

The bore (11) as shown in FIG. 19, which holds the container (13) in the body (4) of the cap (3), can include at least one thread (12), compression means, quick-disconnect means, or inward projection, either alone or in combination, to assist in securing the container (13) to the bore (11). The bore (11) may also include an O-ring or gasket (not shown) to aid in sealing the container (13) to the bore (11) in the body (4) of the cap (3). The bore (11) can also include a screen, mesh, or filter (not shown) to prevent the vaporizable substance (16) from being drawn into or entering the body (4) of the cap (3), through-hole (6), and conduit upon inhalation.

Figure 20:
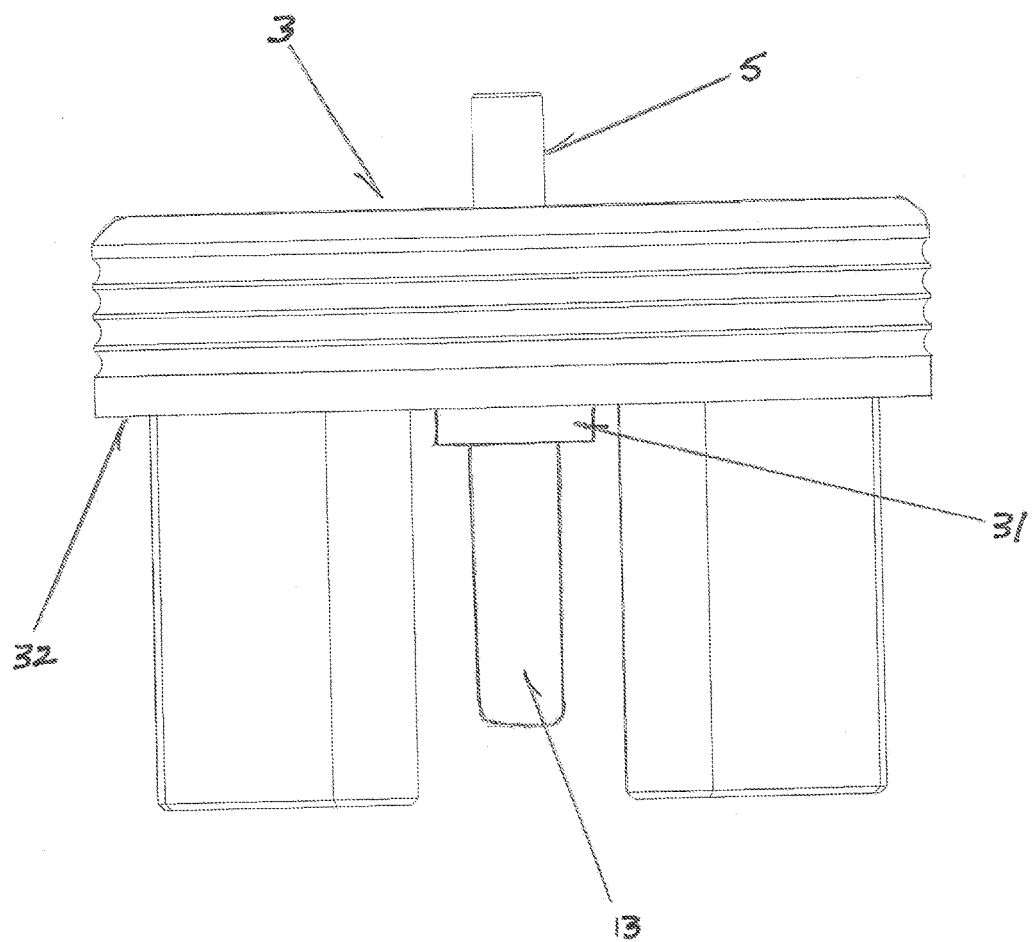
FIG. 20 shows a side view of the cap with an extension platform.

FIG. 20 shows an extension platform (31) located on the bottom surface (32) of the body (4) of the cap (3) that can be provided to adjust the vertical position of the container (13). The extension platform (31) may or may not extend into the housing (2).

Figure 21:
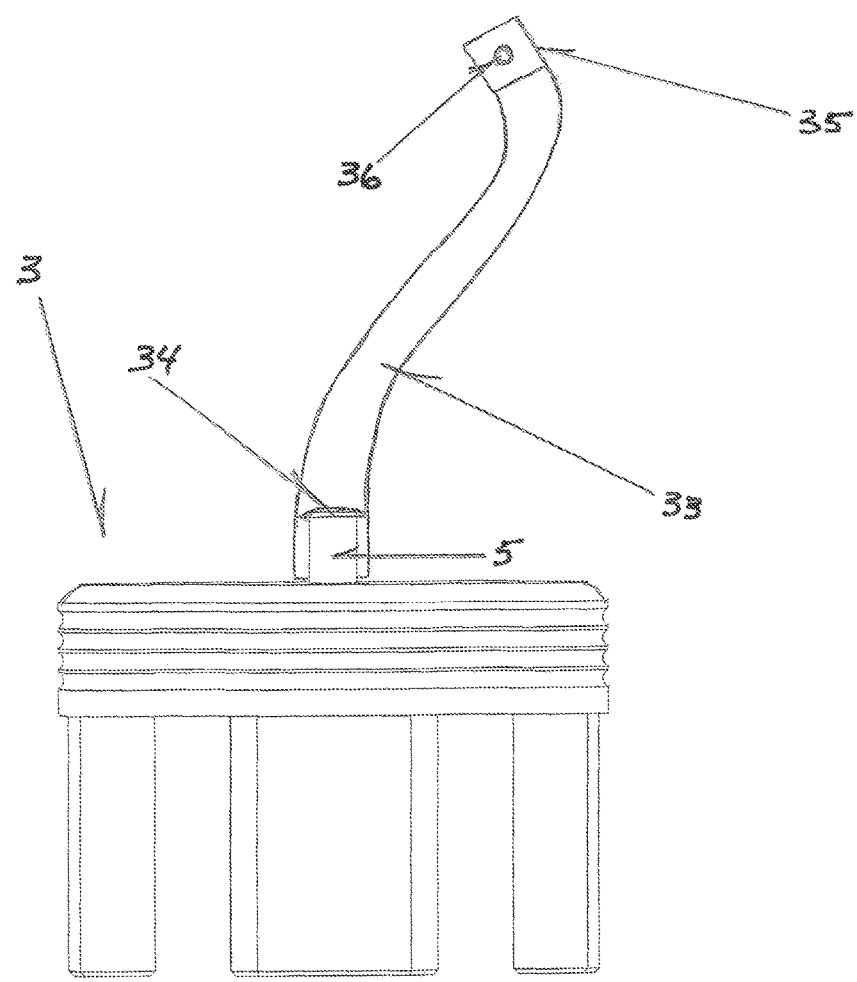
FIG. 21 shows a cap with a flexible conduit attached thereto.
Figure 22:
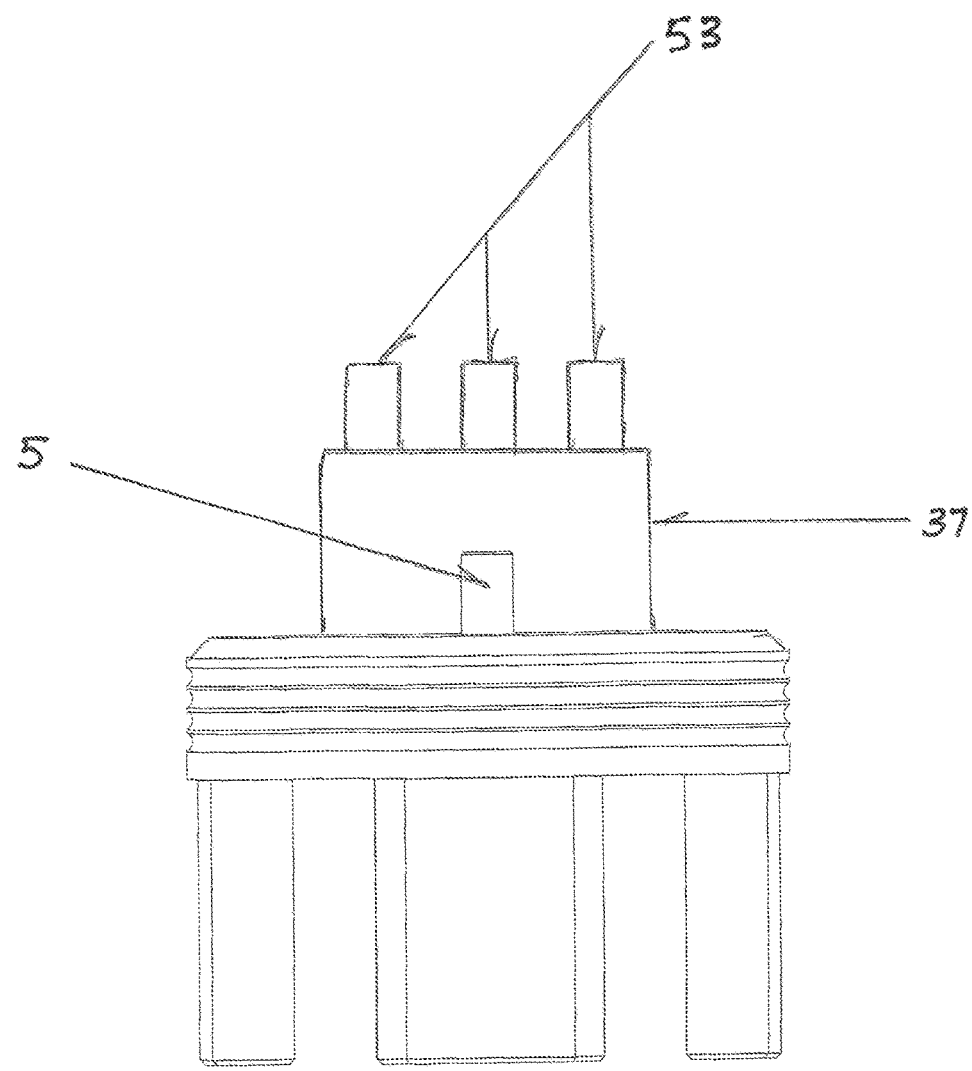
FIG. 22 shows a cap with an attachable manifold having a plurality of nipples for a plurality of conduits.

FIG. 21 shows a flexible conduit (33), which can be a hose made of a material such as silicone, rubber, or polytetrafluoroethylene extending from the nipple (5) of the cap (3). A plurality of nipples (5) may be formed on the cap (3), so that a plurality of flexible conduits (33) may be connected, and multiple users may inhale vapor through the plurality of flexible conduits (33) simultaneously. The nipple (5) may additionally have at least one barb (34) to aid in securing the flexible conduit (33) to the cap (3) or a compression clamp can alternatively be used to tighten the flexible conduit (33) around the nipple (5). A mouthpiece (35) can be inserted into the distal end of the flexible conduit (33) for user comfort. The mouthpiece (35) can also include at least one button (36) to control operation of the vaporization unit (1). When using the cap (3) with a plurality of flexible conduits (33), a manifold (37) with a plurality of manifold nipples (53), as shown in FIG. 22, may be releasably connected to the cap (3) and/or the nipple (5) on the cap (3). The manifold (37) can also be formed integral to the body (4) of the cap (3). The flexible conduit (33) can also comprise an inlet, breathing mask, or nose tube, wherein a gas may be mixed with the vapor to achieve the desired medical purpose.

Figure 23:
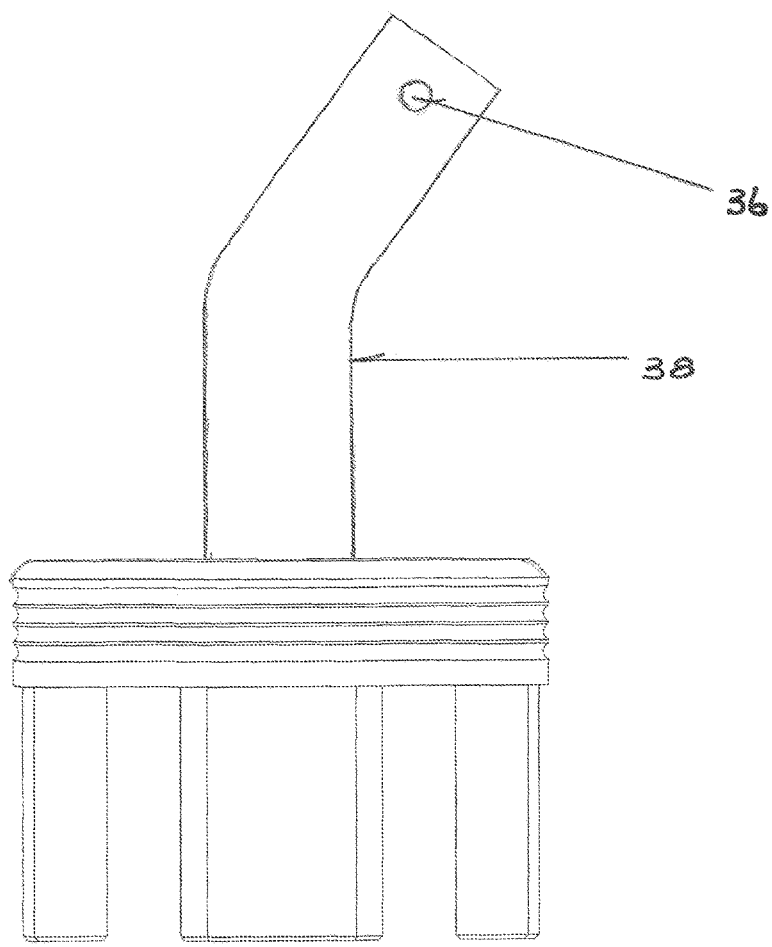
FIG. 23 shows a cap with a rigid pipe-style conduit.

FIG. 23 shows a rigid conduit (38), such as a pipe extension, that can be integrally substituted for the nipple (5) and flexible conduit (33) arrangement of FIG. 21. Alternatively, the rigid conduit (38) can be attached to the cap (3) or nipple (5) through known mechanical attachment means, such as but not limited to quick-disconnect means, press-fit, shrink-fit, interference-fit, snap connection, at least one magnet, at least one clamp, or at least one thread. The rigid conduit (38) can also be attached to the body (4) of the cap (3) by soldering, brazing, welding, adhesives or any other known manner. The rigid conduit (38) can further contain a liquid filtration means (not shown) for cleaning and/or cooling the vapor that passes therethrough. Similar to the flexible conduit (33), the rigid conduit (38) can also include an inlet for the introduction of a gas, such as a medical gas, that is mixed with the vapor.

Figure 24:
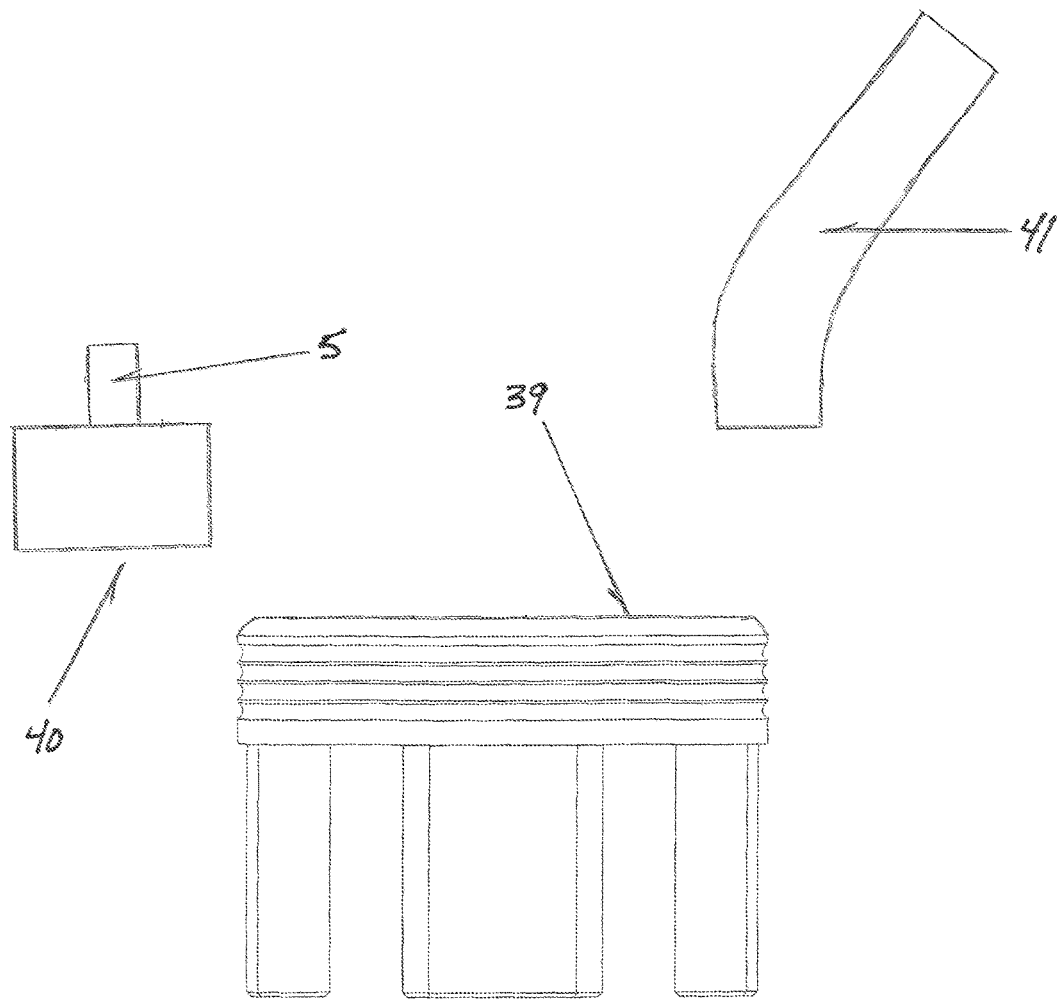
FIG. 24 shows a nippleless cap with a detachable nipple connector and a detachable pipe which may be interchangeable.

FIG. 24 shows a nippleless cap (39) with a detachable nipple connector (40) for use with a flexible conduit (33) and a detachable pipe (41) attachment. In this embodiment, either the detachable nipple connector (40) or detachable pipe (41) can be selectively attached to the nippleless cap (39). This provides the user with the flexibility of using either a flexible (33) or rigid (38) conduit on a nippleless cap (39). The detachable nipple connector (40) and a detachable pipe (41) can also be attached to a cap (3) that has a nipple (5). Connections between the cap (3) or nippleless cap (39) and the detachable nipple connector (40) or detachable pipe (41) are made through known mechanical attachment means, such as but not limited to quick-disconnect means, snap connection, at least one magnet, at least one clamp, or at least one thread.

Figure 25:
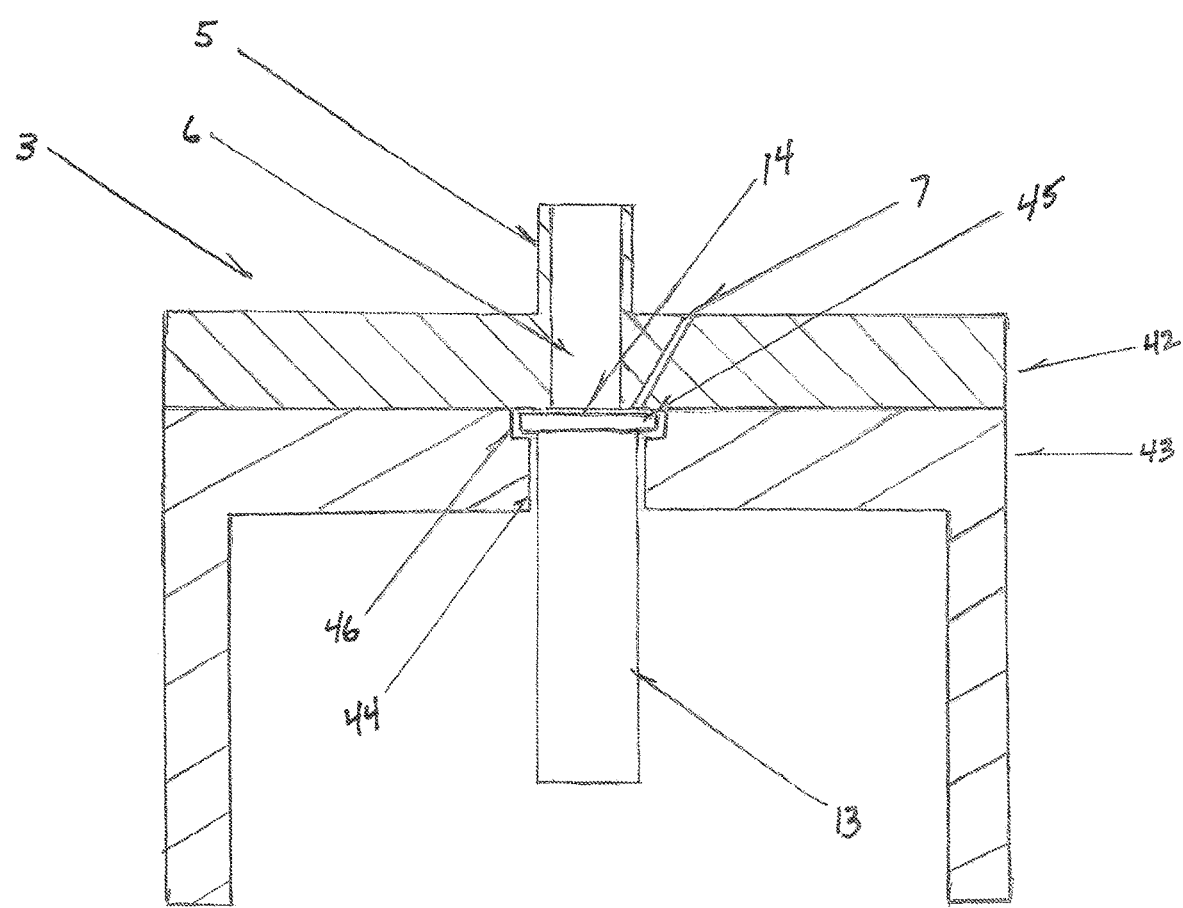
FIG. 25 shows a cross-section of a cap comprising opposing first and second pieces with a flanged container.

FIG. 25 shows a cross-section of another cap (3) embodiment comprising a first opposing piece (42) and a second opposing piece (43) that can be secured to one another to lock a container (13) that is inserted into and through a bore hole (44) of the second opposing piece (43). In this embodiment, it is preferable that the container (13) has a flange (45) proximal the opening (14) of the container (13). When using a flange (45) on the container (13) the bore hole (44) can include a counterbore (46) on which the flange (45) rests.

Figure 26:
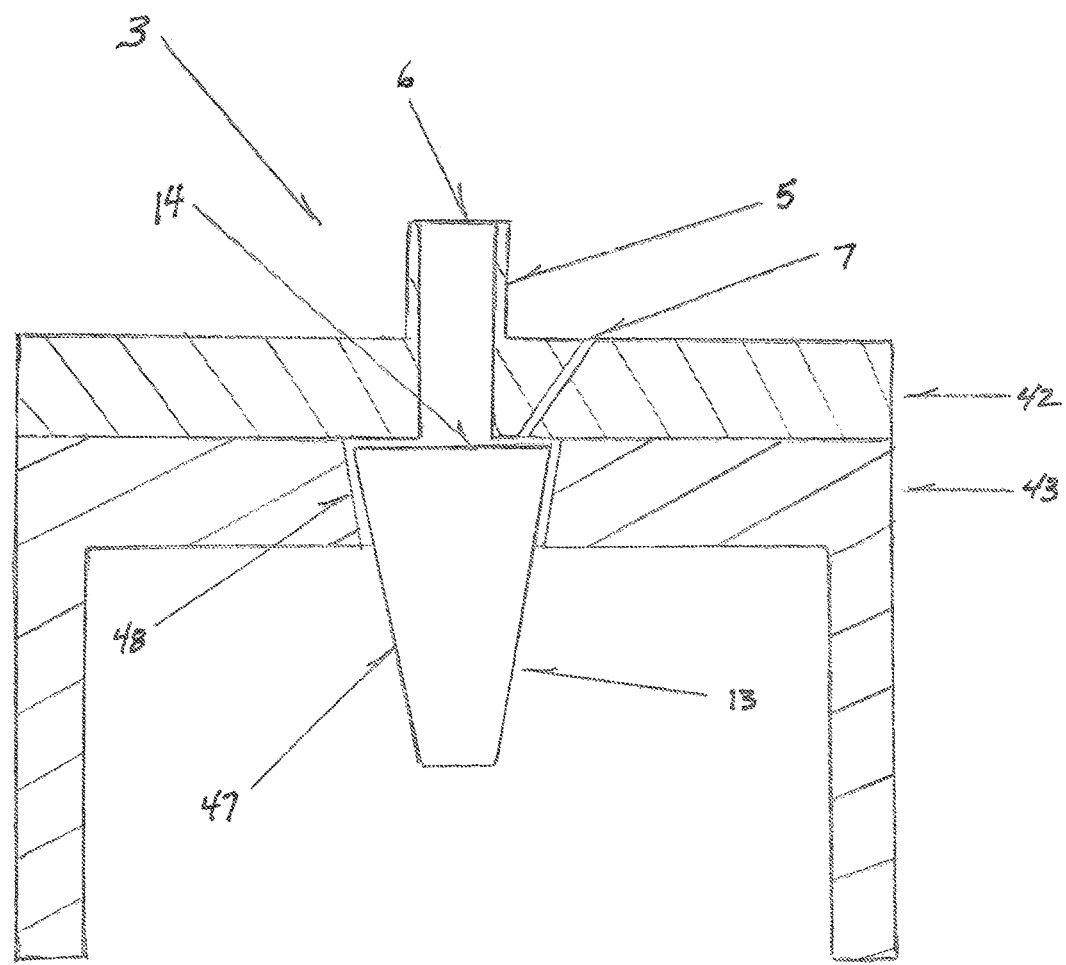
FIG. 26 shows a cross-section of a cap comprising opposing first and second pieces with an angled container.

In another embodiment, as shown in the cross-section of FIG. 26, the container (13) can include an angled side wall (47) with a larger diameter proximal the opening (14) that mates with a corresponding angled bore hole (48). In the embodiments of FIGS. 25-26, the first opposing piece (42) and a second opposing piece (43) can be secured together by complementary threads, magnets, snapped, hinged, clasped, clamped, compression fit, or by any other known mechanical means. When the first opposing piece (42) and a second opposing piece (43) are secured, the first opposing piece (42) can provide a downward force or compression that holds the container (13) and/or flange (45) snuggly in the bore hole (44), counterbore (46), and/or angled bore hole (48).

Figure 27:
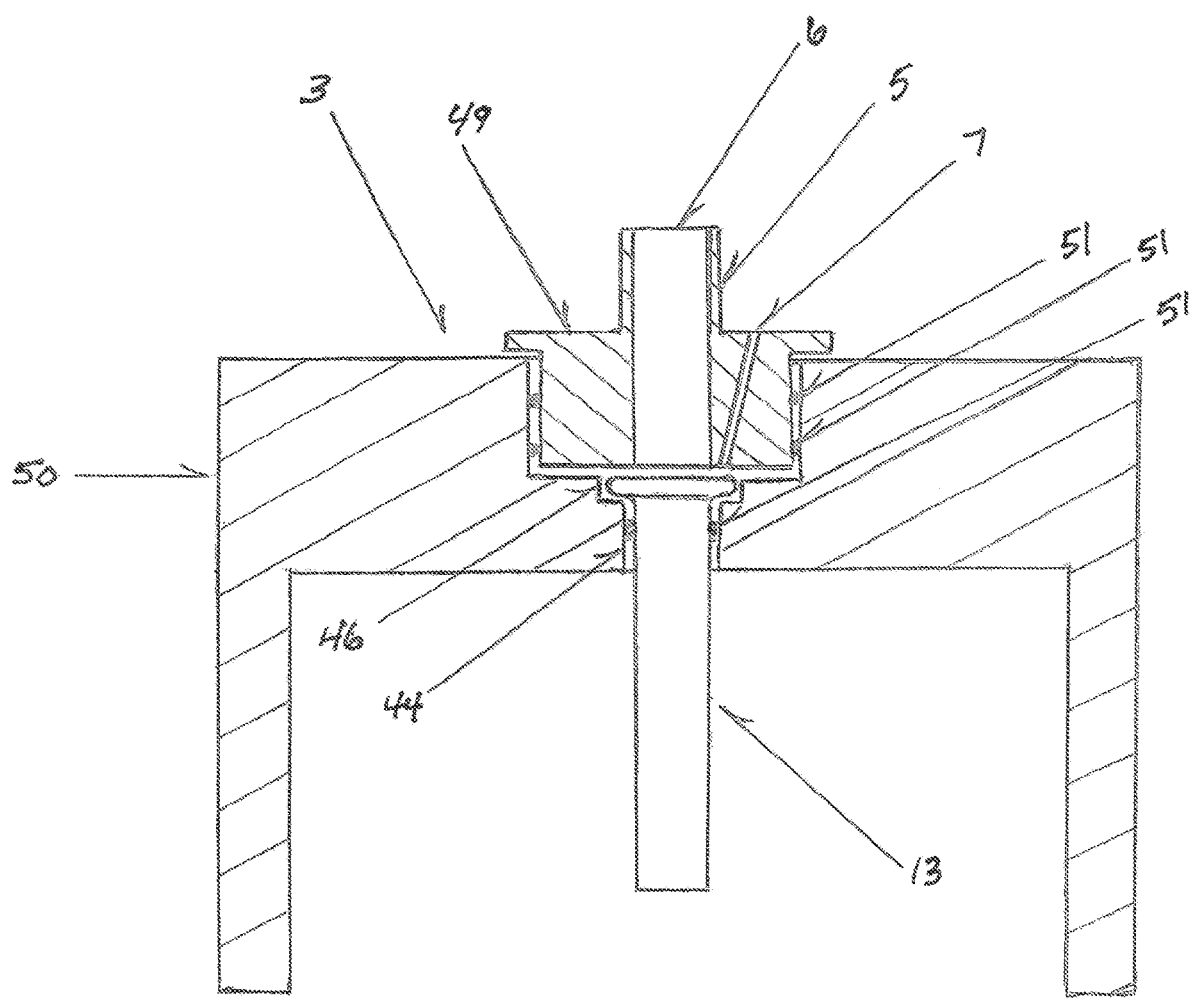
FIG. 27 shows a cross-section of a cap comprising a plug and a lower body.

FIG. 27 shows a cross-section of another embodiment in which the cap (3) comprises a plug (49) that is inserted into a lower body (50), thereby securing the container (13) into bore hole (44) and/or counterbore (46). The plug (49) comprises a nipple (5), a through-hole (6), and at least one vent (7). At least one O-ring (51) can optionally be used to assist in securing and sealing the plug (49) in the lower body (50), and also securing and sealing the container (13) to the lower body (50). The plug (49) in other embodiments can be nippleless and can be attached to flexible (33) and rigid (38) conduits in the manner described above.

Temperature of the vaporization unit (1) can be regulated with a thermal protector, temperature probe, thermocouple, bi-metal sensor, infrared temperature sensor, or laser temperature sensor that measures the temperature of the air at or near the container (13), or the ambient temperature within the housing (2). The temperature of the container (13) and/or susceptor (15) can alternatively be measured by the disclosed means. Power supplied to the induction coil (17) can be controlled by a processor, which provides precise monitoring and control of the power supplied to the induction coil in real-time. The processor is configured to receive data from a temperature sensor and/or a power monitoring circuit and is able to adjust a heating profile applied to the at least one susceptor (15) by the induction coil (17). Induction heating can be automated with a thermal protector or temperature sensor and used in conjunction with a control unit to keep the unit operating within the desired temperature range.

Figure 28:
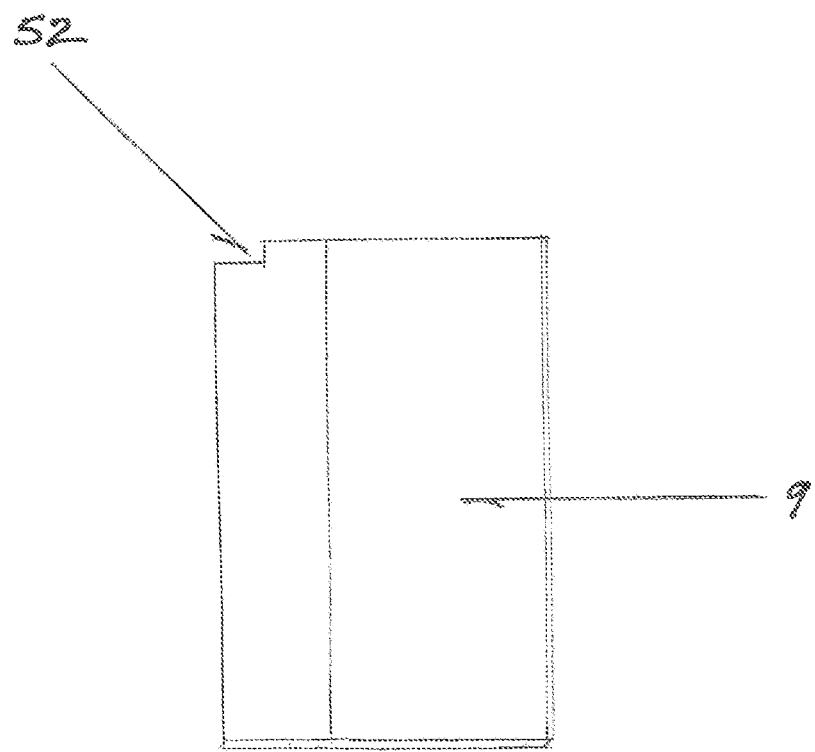
FIG. 28 shows a leg with a locking notch.

FIG. 28 shows a leg (9) with a locking notch (52). After the at least one leg (9) having a locking notch (52) is inserted into at least one opening (26) in the housing (2), the cap (3) can be twisted in a direction so that a portion of the top plate (28) or housing (2) is inserted into at least one locking notch (52). The twisting action locks the cap (3) to the housing (2). The cap (3) can then be removed by twisting the cap (3) in the opposite direction and pulling the at least one leg (9) out of the top plate (28) or housing (2).

Figure 29:
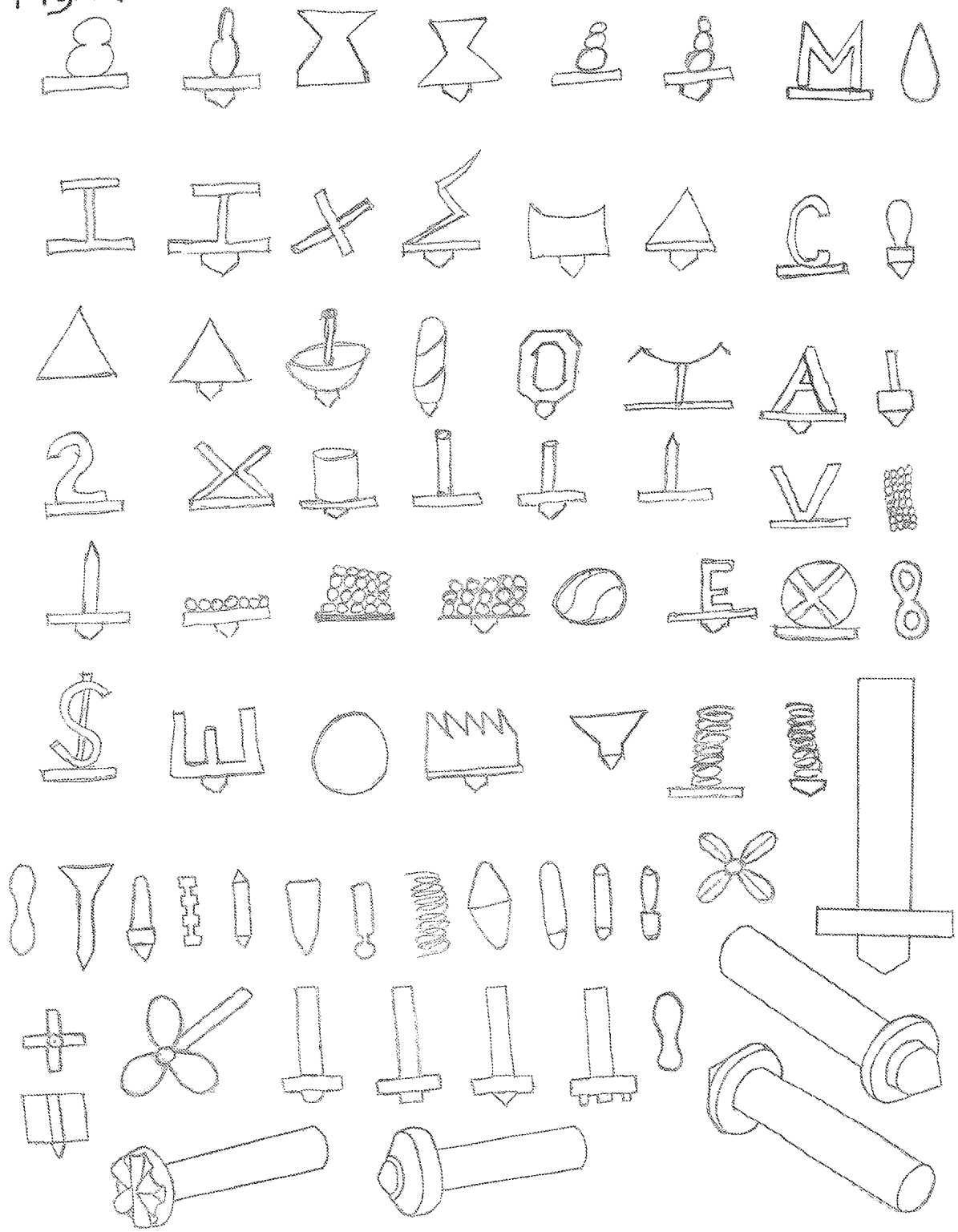
FIG. 29 shows a variety of different susceptors shapes.

FIG. 29 shows a variety of susceptor designs that are usable in the vaporization unit of the present invention.

Figure 30:
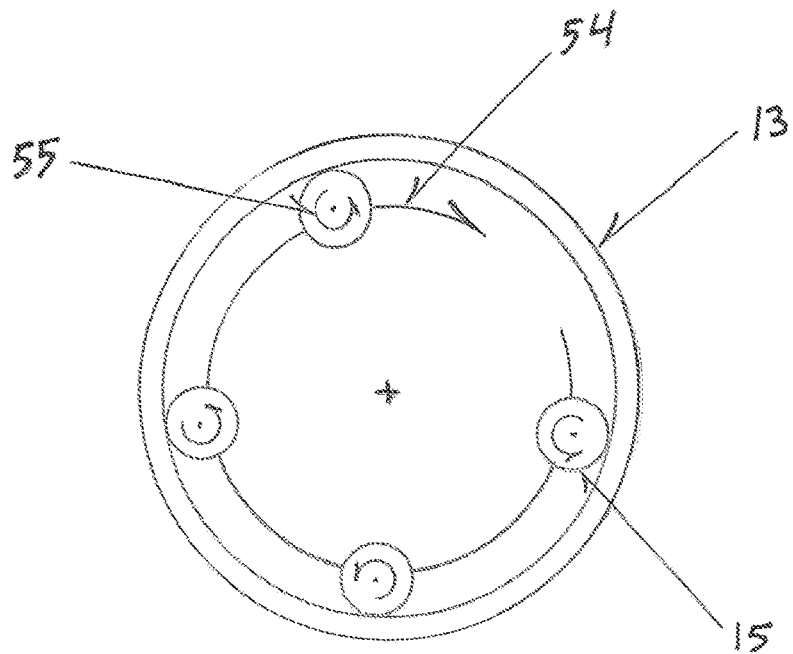
FIG. 30 shows the spinning, rotating, rolling and/or revolving movement of a susceptor as the susceptor moves along the inside wall of a container upon inhalation.

FIG. 30 shows a top view of the container (13) with a single susceptor (15) at different locations when the susceptor (15) is spinning, rotating, rolling, and/or revolving along the inside wall of the container (13) upon inhalation. The susceptor movement described in this paragraph and depicted in FIG. 30 can be achieved with a container comprising a flat interior bottom surface (19), a shaped interior bottom surface (20), or a recess (21). Orbit (54) shows the path and direction the susceptor (15) travels as it revolves around the central vertical axis (+) of the container (13) during inhalation. Rotation direction (55) shows the rotation or rolling movement of the susceptor (15) as it travels on the inside surface of the container (13). The revolving and rolling action of the susceptor (15) occurs simultaneously upon inhalation. The revolving and rolling direction of the susceptor (15) can be reversed simply by changing the direction of the vortex or venturi effect within the container by altering the direction and/or angle of the at least one vent (7). When the susceptor (15) moving around the inside of the container (13) reaches a certain velocity during inhalation, the susceptor (15) lifts off the bottom of the container (13) and moves vertically upward while continuing to ride and roll on the inside surface of the container. During this upward movement the bottom of the susceptor does not contact a flat interior bottom surface, a shaped interior bottom surface, or a recess of the container (13).

Figure 31:
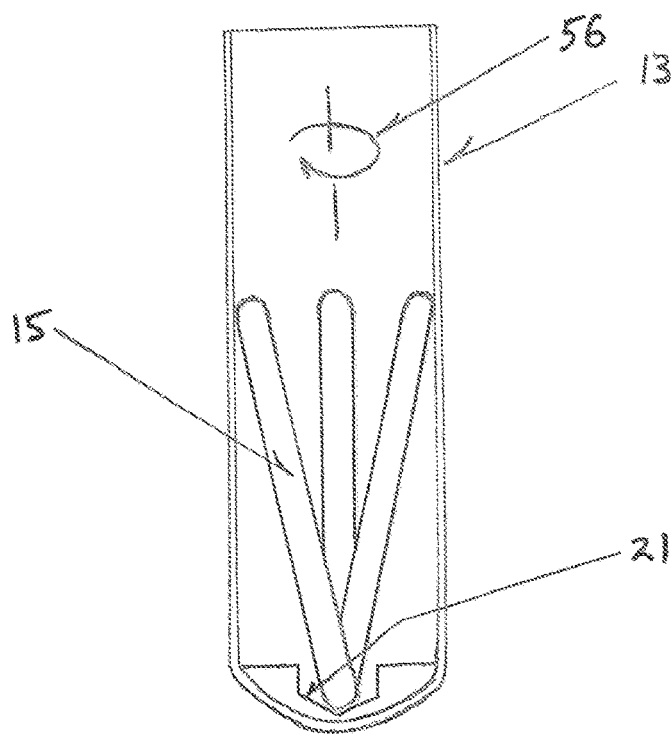
FIG. 31 shows a container with a pointed or conically shaped interior bottom surface forming a recess; and shows the spinning, rotating, rolling and/or revolving movement of a susceptor with the bottom end of the susceptor located in the pointed or conically shaped interior bottom surface (recess) of the container and the upper end of the susceptor contacting the interior surface of the sidewall of the container.

FIG. 31 shows a container (13) with a pointed or conically shaped interior bottom surface forming a recess (21) that compliments and holds a susceptor (15). FIG. 31 also shows the spinning, rotating, rolling and/or revolving movement of a single susceptor (15) at different locations within the container (13), wherein the bottom end of the susceptor (15) is located in the recess (21) of the container (13) and the upper end of the susceptor (15) is contacting the interior sidewall of the container (13). The at least one susceptor (15) is propped at an angle and moves in travel direction (56) within the container (13) upon inhalation, that is, the bottom end of the at least one susceptor (15) spins, rotates, rolls, and/or revolves in recess (21), while the upper end of the at least one susceptor (15) concurrently spins, rotates, rolls, and/or revolves around or on the inside surface of the container (13). This movement can alternatively be described as a twirling motion. The movement shown in FIGS. 30 and 31 is useful to stir the vaporizable substance. At least one solid cylinder, rod, or pin with at least one rounded, radiused and/or pointed end is the preferred susceptor shape for achieving the movement depicted in FIGS. 30 and 31, however, any susceptor that is capable of the described movement may be used. This includes at least one cylinder shaped susceptor without at least one rounded, radiused and/or pointed end. Impeller shaped, fan shaped, propeller shaped susceptors, or susceptors comprising at least one fin, vane or blade are also capable of spinning or rotating within the container upon inhalation.

Figure 32:
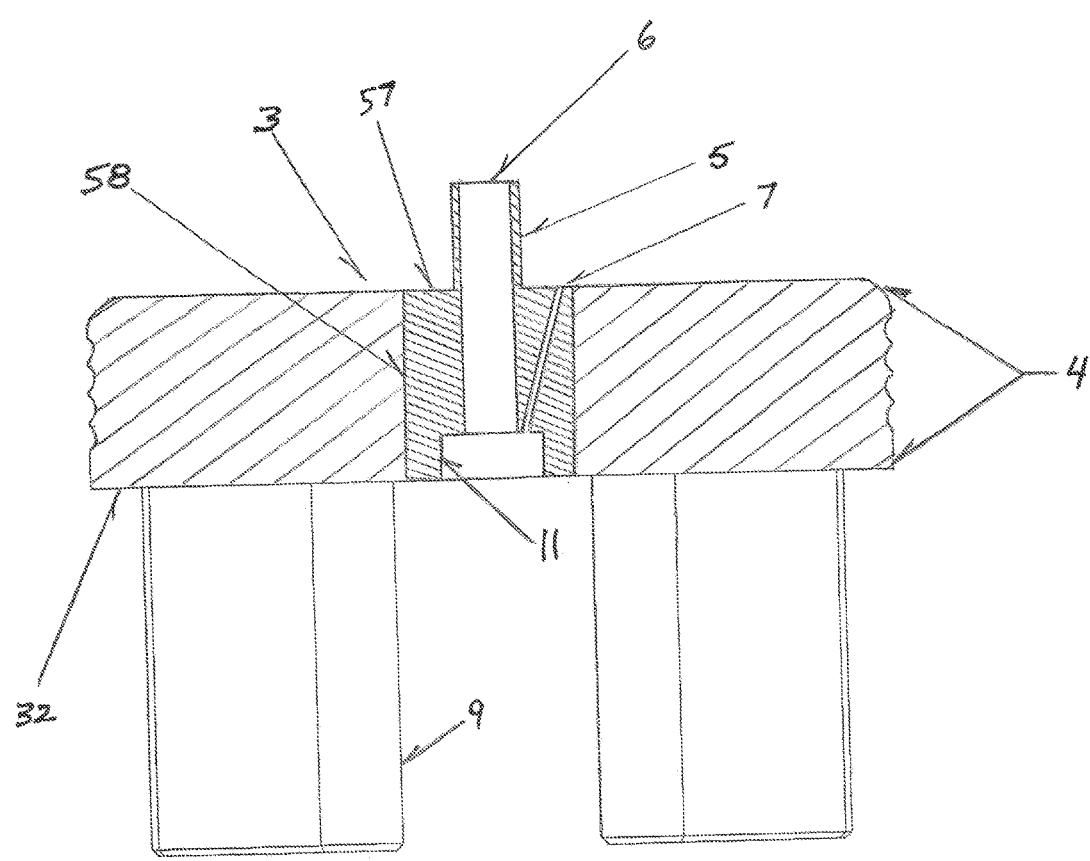
FIG. 32 shows a cross-section of a cap with a central hub inserted therein.
Figure 33:
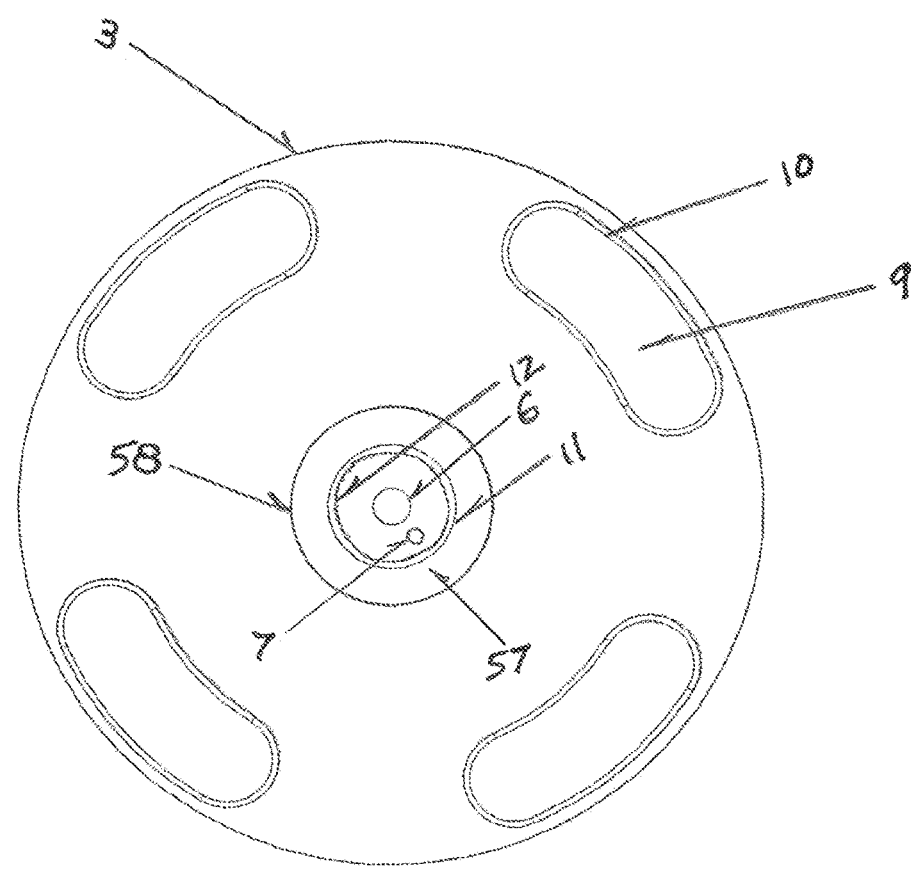
FIG. 33 shows a bottom view of the cap with the central hub inserted therein.

FIG. 32 shows a cross-section view of another embodiment of the cap (3), wherein a central hub (57) is located in the body (4) of the cap (3). The central hub (57) is positioned in a hole (58) of the body (4) of the cap (3) and is attached to the body (4) through a press-fit, shrink-fit, interference-fit, compression-fit, snap connection, quick connect-disconnect, at least one thread, at least one set screw, at least one magnet, at least one clamp, metal or plastic molding process, soldering, brazing, welding, adhesives, or any other known mechanical and/or chemical manner. The hole (58) may or may not extend all the way through the body of the cap (3), and the central hub (57) may partially, fully, or overfill the depth of the hole (58). When at least one thread (not shown) is used to secure the central hub (57) to the body (4) of the cap (3), the at least one thread may be located on the outer surface of the central hub (57) and/or the hole (58) of the body (4) of the cap (3) in which the central hub (57) is inserted. When complimentary threads are used on both the central hub (57) and the body (4) of the cap (3) the threads form a mating engagement. The benefit of this design allows the cap (3) or body (4), and the central hub (57) to be made of different materials. Although the same material may be used for both the cap (3) and central hub (57). For example, the cap (3) comprising a body (4) and at least one leg (9), or the body (4) itself can comprise or be made of a metal, such as aluminum, polymer, monomer, plastic, or wood, while the central hub (57) comprising at least one of: a nipple (5), a through-hole (6), a vent (7), and a bore (11) can comprise or be made of steel, stainless steel such as 304, 304L, 316, or 316L, nickel alloy, titanium, titanium alloy, Grade 2 titanium, glass such as borosilicate or quartz, ceramic, polytetrafluoroethylene, or silicone. Any of the materials listed in this application may be used in any combination to form a cap (3) with a central hub (57). FIG. 33 shows a bottom view of a cap (3) with a central hub (57) inserted therein. The central hub (57) in FIG. 33 has a bore (11) with at least one thread (12) for mating with a threaded end (18) of a container (13), so that the container (13) can be screwed into the central hub (57). In FIGS. 32 and 33 the central hub (57) is cylindrical, however, the central hub (57) can be of any shape.

Figure 34:
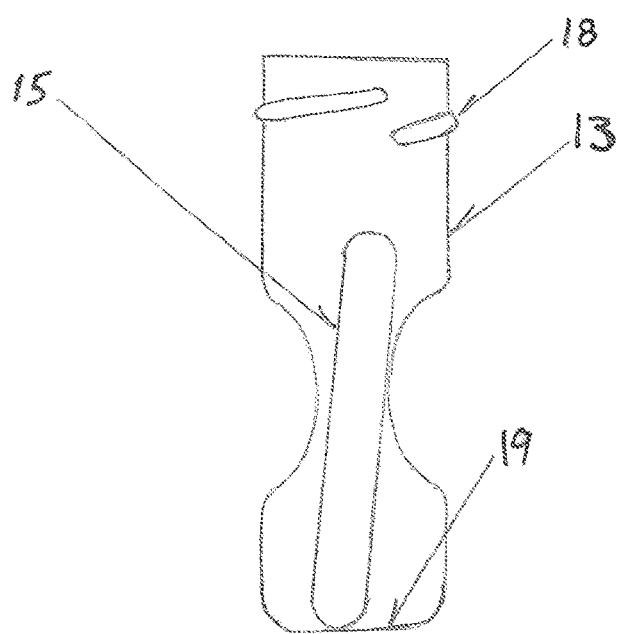
FIGS. 34-37 show a variety of hourglass type containers with various susceptors positioned therein.
Figure 35:
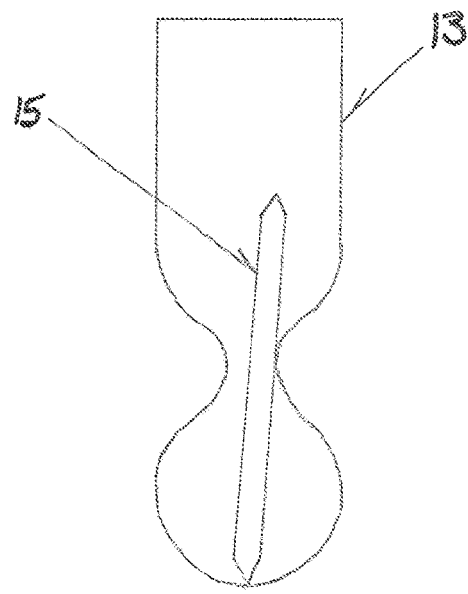
Figure 36:
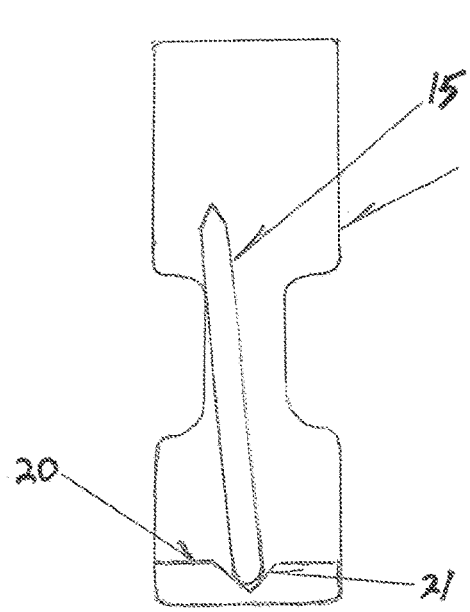
Figure 37:
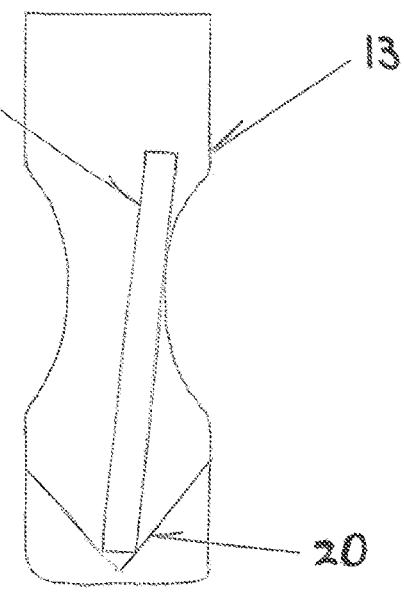

FIGS. 34-37 show hourglass type containers (13) with susceptors (15) positioned therein. The hourglass shaped containers, which have a narrower mid-section than the top and bottom sections of the container, allow at least one susceptor to be substantially vertically and/or axially oriented within the container which promotes more uniform heating of the at least one susceptor. The middle section may be cylindrical or circular like the top and bottom sections, or oblong or elliptical to further promote air turbulence within the container. The shape of the hourglass container can also funnel the vaporizable substance towards the bottom of the container. FIG. 34 shows an hourglass type container (13) with a flat interior bottom surface (19) containing a cylindrical susceptor (15) having rounded ends positioned therein. FIG. 35 shows an hourglass type container (13) having a round lower bulb with a concave shaped interior bottom surface (20) containing a cylindrical susceptor (15) having pointed ends. FIG. 36 shows an hourglass type container (13) having a shaped interior bottom surface (20) with a pointed, v-shaped, triangular prism, pyramid or conical recess (21) containing a cylindrical susceptor (15) having a rounded and a pointed end. FIG. 37 shows an hourglass type container (13) having another variation of a pointed, v-shaped, triangular prism, pyramid or conical shaped interior bottom surface (20) containing a cylindrical susceptor (15).

Figure 38:
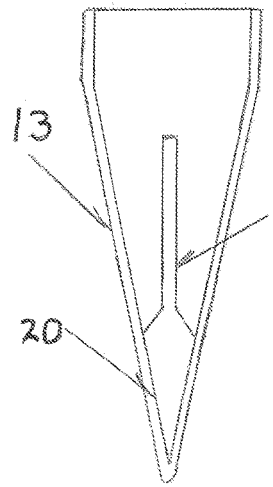
FIGS. 38-45 show variety of containers comprising shaped interior bottom surfaces and various susceptors positioned therein.
Figure 39:
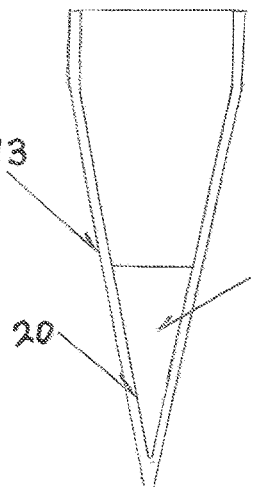
Figure 40:
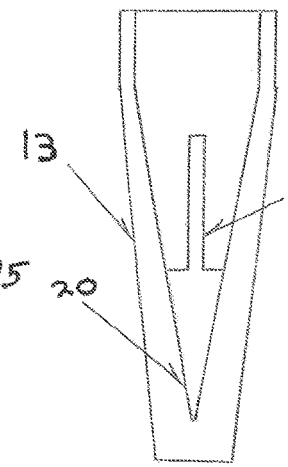
Figure 41:
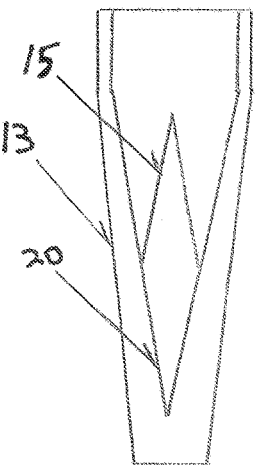
Figure 42:
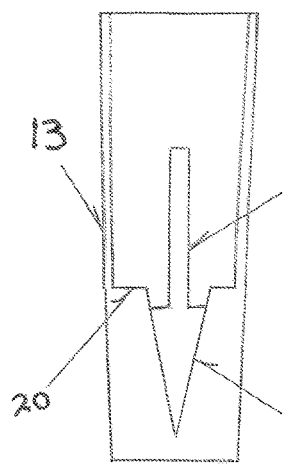
Figure 43:
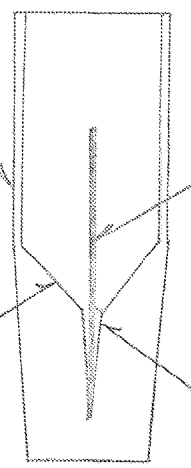
Figure 44:
Figure 45:
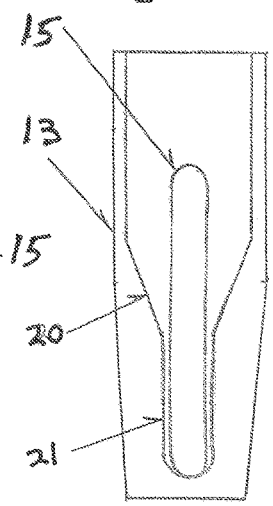

FIGS. 38-45 show a variety of containers (13) having shaped interior bottom surfaces (20) and associated susceptors (15). FIGS. 38-41 show a pointed, v-shaped, triangular prism, pyramid or conically shaped containers (13) with corresponding susceptors (15). The containers (13) are generally round in cross-section so they can be inserted into a circular bore (11) of the cap (3), however, the containers can have three or more distinct sides forming a triangle, square, pentagon, hexagon, heptagon or octagon cross-section. The mating portion of the susceptors (15) in FIGS. 38-42 and 44 is generally pointed, v-shaped, triangular prism, pyramid or conical corresponding to or complimenting a portion of a shaped interior bottom surface (20) and/or recess (21) of the container (13). The mating portion of the susceptor (15) may have three or more distinct sides forming a triangle, square, pentagon, hexagon, heptagon or octagon cross-section corresponding to or complimenting the shaped interior bottom surface (20) and/or recess (21) of the container (13). FIGS. 38-41 and 44 each have a pointed, v-shaped, triangular prism, pyramid or conical shaped interior bottom surface (20). FIGS. 42 and 43 each have a shaped interior bottom surface (20) with a pointed, v-shaped, triangular prism, pyramid or conical recess (21). FIG. 45 has a shaped interior bottom surface (20) with a concave, u-shaped or rounded recess (21) that corresponds to a cylindrical susceptor with rounded ends. FIG. 41 shows a diamond or parallelogram shaped susceptor (15) mating with the shaped interior bottom surface (20) of the container (13). FIG. 43 shows a pin shaped susceptor (15) mating with a recess (21) of the shaped interior bottom surface (20) of the container (13). FIG. 38 shows a spear shaped susceptor (15) and FIG. 44 shows an arrow shaped susceptor (15) mating with the shaped interior bottom surface (20) of the container (13). Various shaped susceptors, such as those described herein, can be designed to mate with either a shaped interior bottom surface (20) or a recess (21) formed in a shaped interior bottom surface (20).

At least one susceptor of any size or a plurality of sizes, any shape or a plurality of shapes, and/or any composition or a plurality of compositions disclosed herein can be used in combination with any of the disclosed container shapes, compositions, interior bottom surfaces, and/or recesses for obtaining the desired heating profile and vapor consistency.

LIST OF ITEMS

Vaporization unit (1)
Housing (2)
Cap (3)
Body (4)
Nipple (5)
Through-hole (6)
Vent hole (7)
Ribs/grooves or Texture (8)
Leg (9)
Chamfer (10)
Bore (11)
Thread (12)
Container (13)
Container opening (14)
Susceptor (15)
Vaporizable substance (16)
Induction coil (17)
Threaded end of container (18)
Flat interior bottom surface (19)
Shaped interior bottom surface (20)
Recess (21)
Pointed or conical tip (22) of susceptor
Sidewall (23) of the container
Floor (24) of susceptor
Direction of gravity (25)
Outer opening(s) (26) in the top plate or housing for the insertion of at least one leg
Central opening (27) in the top plate or housing for the insertion of the container
Top plate (28)
Cavity (29)
Induction unit (30)
Extension platform (31)
Bottom surface (32) of the body of the cap
Flexible conduit (33)
Barb (34)
Mouthpiece (35)
Button (36)
Manifold (37)
Rigid conduit (38)
Nippleless cap (39)
Detachable nipple connector (40)
Detachable pipe (41)
First opposing piece (42)
Second opposing piece (43)
Bore hole (44)
Flange of the container (45)
Counterbore (46)
Angled sidewall (47)
Angled bore hole (48)
Plug (49)
Lower body (50)
O-ring (51)
Locking notch (52)
Manifold nipples (53)
Orbit (54)
Rotation direction (55)
Central vertical axis (+)
Travel direction (56)
Central hub (57)
Hole (58)

The invention claimed is:

1. A vaporizer, comprising:
a cap having at least one leg;
a container attached to the cap;
the container containing at least one susceptor, wherein the container and the at least one susceptor are at least partially located within an induction coil; and
a plate or a housing having at least one opening in which the at least one leg and the container are inserted.

2. The vaporizer of claim 1 wherein the cap further comprises at least one vent through which air is drawn, wherein the at least one vent is in communication with an opening of the container; and
a through-hole through which vapor is drawn, wherein the through-hole is in communication with the opening of the container.

3. The vaporizer of claim 1 wherein the cap further comprises at least one nipple configured for attachment to at least one conduit, and a bore configured to receive the container.

4. The vaporizer of claim 1 wherein the cap further comprises a central hub, wherein the central hub comprises at least one vent through which air is drawn, wherein the at least one vent is in communication with an opening of the container; and
a through-hole through which vapor is drawn, wherein the through-hole is in communication with the opening of the container.

5. The vaporizer of claim 4 wherein the central hub further comprises at least one nipple configured for attachment to at least one conduit, and a bore configured to receive the container.

6. The vaporizer of claim 1 wherein the container further comprises a shaped interior bottom surface or a recess configured to hold the at least one susceptor.

7. The vaporizer of claim 6 wherein the shaped interior bottom surface or the recess of the container is pointed or conically shaped.

8. The vaporizer of claim 1 wherein the at least one susceptor is shaped and configured to spin, rotate, roll, revolve or move up and down inside the container during inhalation.

9. The vaporizer of claim 1 wherein the at least one susceptor is located in a shaped interior bottom surface or a recess of the container.

10. The vaporizer of claim 1 wherein the at least one susceptor is located in a shaped interior bottom surface or a recess of the container, and the at least one susceptor is substantially vertically and/or axially aligned in the container and/or the induction coil.

11. The vaporizer of claim 1 wherein a bottom end of the at least one susceptor is located in a shaped interior bottom surface or a recess of the container, and an upper end of the at least one susceptor is propped at an angle against an inside surface of the container.

12. The vaporizer of claim 1 wherein the at least one susceptor comprises an upper cylindrical shaft, a cylindrical disc, a lower cylindrical shaft, and a conical tip; and wherein the upper cylindrical shaft is longer than the lower cylindrical shaft, and the cylindrical disc has a diameter larger than the upper cylindrical shaft and the lower cylindrical shaft.

13. The vaporizer of claim 1 wherein the at least one opening of the plate or the housing further comprises at least one outer opening configured for insertion of the at least one leg, and a central opening configured for insertion of the container.

14. The vaporizer of claim 1 wherein the plate or the housing further comprises a cavity that receives a body of the cap.

15. The vaporizer of claim 1 wherein the at least one leg of the cap extends farther from a bottom surface of a body of the cap than the container extends from the bottom surface of the body of the cap.

16. A method of vaporizing a substance, comprising:
placing at least one susceptor and the substance into a container;
attaching the container to a cap having at least one leg;
inserting the at least one leg of the cap and the container through at least one opening of a plate or a housing such that the container and the at least one susceptor are at least partially located within an induction coil; and
heating the substance.

17. The method of claim 16 further comprising inhaling through a conduit;
drawing air through at least one vent hole of the cap which is in communication with an opening of the container;
mixing the air drawn through the at least one vent inside the container with the heated substance to form a vapor; and
drawing the vapor through a through-hole of the cap which is in communication with the opening in the container.

18. The method of claim 16 further comprising inhaling through a conduit;
drawing air through at least one vent hole of a central hub of the cap which is in communication with an opening of the container;
mixing the air drawn through the at least one vent inside the container with the heated substance to form a vapor; and
drawing the vapor through a through-hole of the central hub of the cap which is in communication with the opening in the container.

19. The method of claim 16 wherein inserting the at least one leg of the cap and the container through the at least one opening of the plate or the housing further comprises inserting the at least one leg of the cap through at least one outer opening of the plate or the housing, and inserting the container through a central opening of the plate or the housing.

20. The method of claim 16 wherein inserting the at least one leg of the cap and the container through the at least one opening of the plate or the housing further comprises inserting the at least one leg of the cap into the least one opening of the plate or the housing before inserting the container through the at least one opening of the plate or the housing.

21. The method of claim 16 wherein inserting the at least one leg of the cap and the container through the at least one opening of the plate or the housing further comprises inserting a body of the cap into a cavity of the plate or the housing.

22. The method of claim 16 further comprising attaching at least one conduit to at least one nipple of the cap, and attaching the container to the cap by inserting the container into a bore of the cap.

23. The method of claim 16 further comprising inhaling on a conduit so that the at least one susceptor spins, rotates, rolls, revolves or moves up and down inside the container.

24. The method of claim 16 wherein placing the at least one susceptor into the container further comprises inserting or mating the at least one susceptor within a shaped interior bottom surface or a recess of the container.

25. The method of claim 16 wherein placing the at least one susceptor into the container further comprises inserting the susceptor into a shaped interior bottom surface or a recess of the container so the at least one susceptor is substantially vertically and/or axially aligned within the container and/or the induction coil.

26. The method of claim 16 wherein placing the at least one susceptor into the container further comprises inserting a bottom end of the at least one susceptor into a shaped interior bottom surface or a recess of the container, and propping an upper end of the least one susceptor at an angle against an inside surface of the container.

* * * * *